United States Patent
Fukuzawa

(10) Patent No.: US 11,465,150 B2
(45) Date of Patent: Oct. 11, 2022

(54) REACTION TREATMENT DEVICE AND METHOD FOR CONTROLLING REACTION TREATMENT DEVICE

(71) Applicant: Nippon Sheet Glass Company, Limited, Tokyo (JP)

(72) Inventor: Takashi Fukuzawa, Machida (JP)

(73) Assignee: Nippon Sheet Glass Company, Limited, Tokyo (JP)

(*) Notice: Subject to any disclaimer, the term of this patent is extended or adjusted under 35 U.S.C. 154(b) by 812 days.

(21) Appl. No.: 16/192,934

(22) Filed: Nov. 16, 2018

(65) Prior Publication Data

US 2019/0099759 A1 Apr. 4, 2019

Related U.S. Application Data

(63) Continuation of application No. PCT/JP2017/018294, filed on May 16, 2017.

(30) Foreign Application Priority Data

May 18, 2016 (JP) ............... JP2016-099872

(51) Int. Cl.
*B01L 7/00* (2006.01)
*C12M 1/00* (2006.01)
(Continued)

(52) U.S. Cl.
CPC ............ *B01L 7/525* (2013.01); *C12M 1/00* (2013.01); *C12Q 1/686* (2013.01); *B01L 2300/18* (2013.01); *C12N 15/09* (2013.01)

(58) Field of Classification Search
CPC ............ B01L 7/525; B01L 2300/18; B01L 2200/147; B01L 2300/1822;
(Continued)

(56) References Cited

U.S. PATENT DOCUMENTS

2008/0003588 A1* 1/2008 Hasson ............... B01L 3/50273
435/6.11
2010/0267017 A1 10/2010 Hassard
(Continued)

FOREIGN PATENT DOCUMENTS

CN 202099269 U 1/2012
CN 103201633 A 7/2013
(Continued)

OTHER PUBLICATIONS

International Search Report dated Aug. 15, 2017 issued by the International Searching Authority in PCT/JP2017/018294.
(Continued)

*Primary Examiner* — Liban M Hassan
(74) *Attorney, Agent, or Firm* — Sughrue Mion, PLLC

(57) ABSTRACT

A reaction processor is provided with a reaction processing vessel having a channel, a liquid feeding system, a temperature control system, and a fluorescence detector, and a CPU for controlling the liquid feeding system. When a sample moves from a low temperature region to a high temperature region, the CPU instructs the liquid feeding system to stop the sample when a predetermined first waiting time has passed from the time when the passage of the sample through a fluorescence detection region is detected by the fluorescence detector. When the sample moves from the high temperature region to the low temperature region, the CPU instructs the liquid feeding system to stop the sample when a predetermined second waiting time, which is set independently of the first waiting time, has passed from the time when the passage of the sample through the fluorescence detection region is detected by the fluorescence detector.

9 Claims, 7 Drawing Sheets

(51) Int. Cl.
*C12Q 1/686* (2018.01)
*C12N 15/09* (2006.01)

(58) Field of Classification Search
CPC .... B01L 2300/1827; B01L 2400/0487; C12M 1/00; C12Q 1/686; C12N 15/09
USPC .......................................... 435/287.2, 289.1
See application file for complete search history.

(56) References Cited

U.S. PATENT DOCUMENTS

| 2012/0178091 | A1* | 7/2012 | Glezer .................... | B01L 7/525 |
| | | | | 435/6.12 |
| 2014/0272992 | A1* | 9/2014 | Drummond ............ | C12Q 1/686 |
| | | | | 435/6.12 |
| 2017/0130261 | A1* | 5/2017 | Nagai ............... | B01L 3/502715 |

FOREIGN PATENT DOCUMENTS

| CN | 103635568 A | 3/2014 |
| CN | 104263634 A | 1/2015 |
| CN | 105154326 A | 12/2015 |
| EP | 3 385 365 A1 | 10/2018 |
| JP | 2009-517075 A | 4/2009 |
| JP | 2009-232700 A | 10/2009 |
| WO | 2016/006612 A1 | 1/2016 |

OTHER PUBLICATIONS

International Preliminary Report on Patentability with the translation of Written Opinion dated Nov. 29, 2018 issued by the International Bureau in PCT/JP2017/018294.
Office Action dated May 18, 2021 in Japanese Application No. 2019-134429.
Office Action dated May 12, 2021 in Chinese Application No. 201780028824.1.
Communication dated Dec. 6, 2019, from the European Patent Office in counterpart European Application No. 17799357.3.
Jeff Chiou, et al., "A closed-cycle capillary polymerase chain reaction machine", Analytical Chemistry, American Chemical Society, May 1, 2001, vol. 73, No. 9, pp. 2018-2021 (4 pages total).
Search Report dated Sep. 15, 2020 from the Taiwan Intellectual Property Office in Application No. 106116347.
Communication dated Aug. 31, 2021 from the Indian Intellectual Property Office in Application No. 201817043665.
Communication dated Oct. 15, 2019, from the Intellectual Property Office of Singapore in counterpart application No. 11201810224S.

* cited by examiner

FIG. 3A  DISTANCE X (STOPPING POSITION OF SAMPLE)
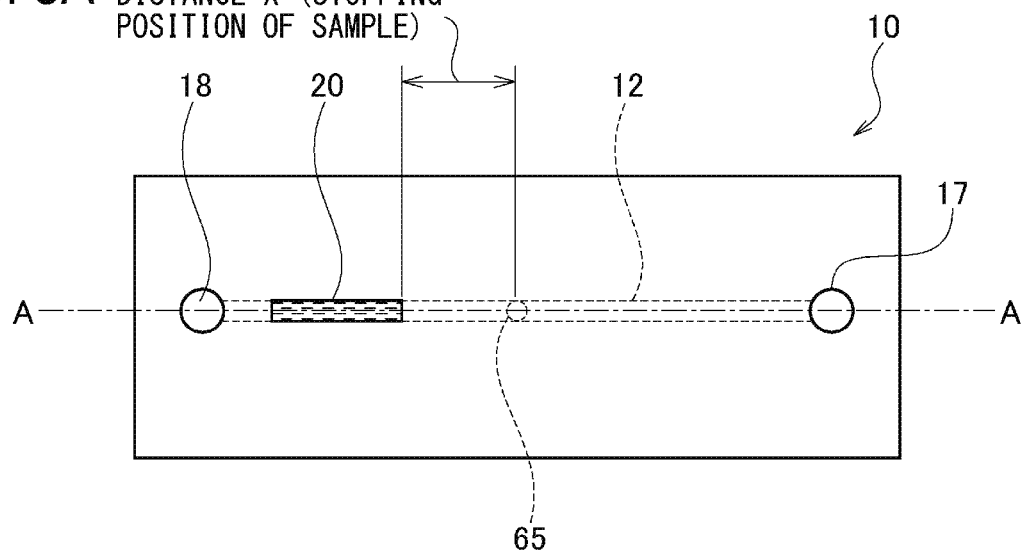
FIG. 3B
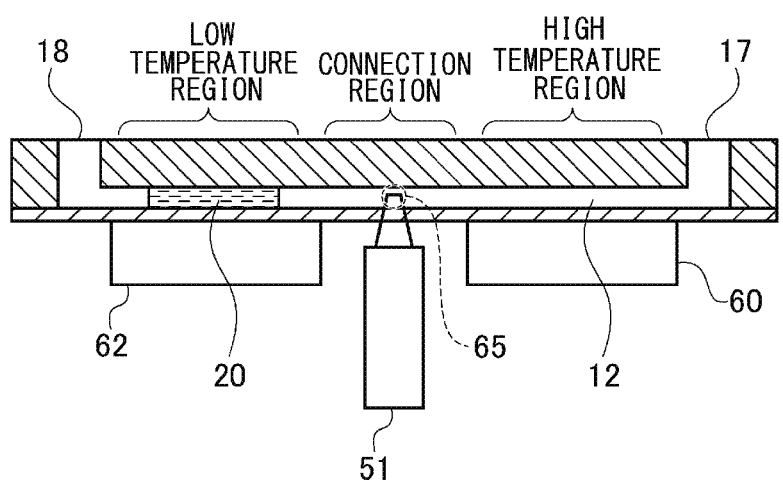

REACTION TREATMENT DEVICE AND METHOD FOR CONTROLLING REACTION TREATMENT DEVICE

CROSS-REFERENCE TO RELATED APPLICATIONS

This application is a Continuation of PCT International Application No. PCT/JP2017/018294 filed on May 16, 2017, which claims priority under 35 U.S.C. § 119(a) to Japanese Patent Application No. 2016-099872, filed on May 18, 2016.

BACKGROUND OF THE INVENTION

1. Field of the Invention

The present invention relates to reaction processors used for polymerase chain reactions (PCR) and methods for controlling the reaction processors.

BACKGROUND ART

Genetic testing is widely used for examinations in a wide variety of medical fields, identification of farm products and pathogenic microorganisms, safety assessment for food products, and even for examinations for pathogenic viruses and a variety of infectious diseases. In order to detect with high sensitivity a minute amount of gene's DNA, methods of analyzing the resultant obtained by amplifying a portion of DNA are known. Above all, PCR is a remarkable technology where a certain portion of a very small amount of DNA collected from an organism or the like is selectively amplified.

In PCR, a predetermined thermal cycle is applied to a sample in which a biological sample containing DNA and a PCR reagent consisting of primers, enzymes, and the like are mixed so as to cause denaturation, annealing, and elongation reactions to be repeated so that a specific portion of DNA is selectively amplified.

It is a common practice to perform PCR by putting a predetermined amount of a target sample into a PCR tube or a reaction processing vessel such as a microplate (microwell) in which a plurality of holes are formed. However, in recent years, PCR using a reaction processing vessel (also referred to as "chip") provided with a micro-channel that is formed on a substrate is practiced (e.g. Patent Document 1).

[Patent Document 1] Japanese Patent Application Publication No. 2009-232700

SUMMARY OF THE INVENTION

In PCR using a reaction vessel of a reciprocating channel type, in order to apply a thermal cycle to a sample by moving the sample in a reciprocating manner in a channel, a plurality of temperature regions each maintained at a different temperature are set on the channel. In order to properly apply a thermal cycle to a sample, it is necessary for the sample to stop accurately in each temperature region. Variations in the stopping position may prevent reactions from occurring, cause the progress of reactions to vary according to the location of the sample, and cause reactions such as amplification of DNA to be inaccurate, which may lead to erroneous judgment by workers and/or those engaged in the work.

In this background, a purpose of the present invention is to provide a technology capable of precisely stopping a sample at a predetermined position in a temperature region in a reaction processor capable of applying a thermal cycle to the sample by moving the sample in a reciprocating manner in a channel in which different temperature regions are set.

A reaction processor according to one embodiment of the present invention comprises: a reaction processing vessel in which a channel where a sample moves is formed; a liquid feeding system that moves and stops the sample in the channel; a temperature control system that provides a first temperature region maintained at a first temperature and a second temperature region maintained at a second temperature lower than the first temperature in the channel; a detection system that detects the sample passing through a detection region that is set between the first temperature region and the second temperature region of the channel; and a control unit that controls the liquid feeding system based on a signal detected by the detection system. When the sample moves from the second temperature region to the first temperature region, the control unit instructs the liquid feeding system to stop the sample when a predetermined first waiting time has passed from the time when the passage of the sample through the detection region is detected by the detection system. When the sample moves from the first temperature region to the second temperature region, the control unit instructs the liquid feeding system to stop the sample when a predetermined second waiting time, which is set independently of the first waiting time, has passed from the time when the passage of the sample through the detection region is detected by the detection system.

Another embodiment of the present invention also relates to a reaction processor.

This reaction processor comprises: a reaction processing vessel in which a channel where a sample moves is formed; a liquid feeding system that moves and stops the sample in the channel; a temperature control system that provides a first temperature region maintained at a first temperature and a second temperature region maintained at a second temperature lower than the first temperature in the channel; a detection system that detects the sample passing through a detection region that is set between the first temperature region and the second temperature region of the channel; and a control unit that controls the liquid feeding system based on a signal detected by the detection system. Given that: when the sample moves from the second temperature region to the first temperature region, the moving speed of the sample in the detection region is denoted as a first moving speed $v_1$, and the distance between an end portion of the sample stopping at a predetermined position in the channel that is closest to the detection region and the center of the detection region is denoted as $X_{01}$; when the sample moves from the first temperature region to the second temperature region, the moving speed of the sample in the detection region is denoted as a second moving speed $v_2$, and the distance between an end portion of the sample stopping at a predetermined position in the channel that is closest to the detection region and the center of the detection region is denoted as $X_{02}$; and when a fixed period of time specific to the reaction processor is denoted as $t_c$, the control unit instructs the liquid feeding system to stop the sample when a first waiting time defined by $t_{d2/1} = X_{01}/v_1 - t_c$ has passed when the sample moves from the second temperature region to the first temperature region and when a second waiting time defined by $t_{d2/2} = X_{02}/V_2 - t_c$ has passed when the sample moves from the first temperature region to the second temperature region.

Another embodiment of the present invention also relates to a reaction processor. This reaction processor comprises: a reaction processing vessel in which a channel where a sample moves is formed; a liquid feeding system that moves and stops the sample in the channel; a temperature control system that provides a first temperature region maintained at a first temperature and a second temperature region maintained at a second temperature lower than the first temperature in the channel; a detection system that detects the sample passing through a detection region that is set between the first temperature region and the second temperature region of the channel; and a control unit that controls the liquid feeding system based on a signal detected by the detection system. Given that: when the sample moves from the second temperature region to the first temperature region, the moving speed of the sample in the detection region is denoted as a first moving speed $v_1$, and the distance between an end portion of the sample stopping at a predetermined position in the channel that is closest to the detection region and the center of the detection region is denoted as $X_{01}$; when the sample moves from the first temperature region to the second temperature region, the moving speed of the sample in the detection region is denoted as a second moving speed $v_2$, and the distance between an end portion of the sample stopping at a predetermined position in the channel that is closest to the detection region and the center of the detection region is denoted as $X_{02}$; and when a fixed period of time specific to the reaction processor is denoted as $t_c$, and a and R are defined as correction coefficients, the control unit instructs the liquid feeding system to stop the sample when a first waiting time defined by $t_{d2/1}=\alpha*(X_{01}/v_1)-t_c$ has passed when the sample moves from the second temperature region to the first temperature region and when a second waiting time defined by $t_{d2/2}=\beta*(X_{02}/v_2)-t_c$ has passed when the sample moves from the first temperature region to the second temperature region.

$t_c$ may be time corresponding to the difference between the time when the sample has actually passed through the detection region and the time when the detection system has detected the passage of the sample through the detection region.

The sample may include DNA, a PCR reagent, and a reagent that emits fluorescence. The detection system may include a fluorescence detector for detecting fluorescence emitted from the sample. Given that: the time the sample takes to pass through the detection region when the sample moves from the second temperature region to the first temperature region is denoted as a first transit time $t_{p1}$; and the time the sample takes to pass through the detection region when the sample moves from the first temperature region to the second temperature region is denoted as a second transit time $t_{p2}$, the control unit may obtain the first transit time $t_{p1}$ and the second transit time $t_{p2}$ based on the signal from the fluorescence detector or a value obtained by performing predetermined arithmetic processing on the signal and on a predetermined threshold value, and the control unit may calculate the first moving speed $v_1=L/t_{p1}$ based on the first transit time $t_{p1}$ and the length L of the sample and the second moving speed $v_2=L/t_{p2}$ based on the second transit time $t_{p2}$ and the length L of the sample.

The control unit may change the threshold value according to the progress of the reaction of the sample.

The control unit may control the liquid feeding system such that the first transit time $t_{p1}$ and the second transit time $t_{p2}$ become predetermined target transit times.

Still another embodiment of the present invention relates to a method for controlling a reaction processor that comprises: a reaction processing vessel in which a channel where a sample moves is formed; a liquid feeding system that moves and stops the sample in the channel; a temperature control system that provides a first temperature region maintained at a first temperature and a second temperature region maintained at a second temperature lower than the first temperature in the channel; and a detection system that detects the sample passing through a detection region that is set between the first temperature region and the second temperature region of the channel. This method comprises: instructing, when the sample moves from the second temperature region to the first temperature region, the liquid feeding system to stop the sample when a predetermined first waiting time has passed from the time when the passage of the sample through the detection region is detected by the detection system, and instructing, when the sample moves from the first temperature region to the second temperature region, the liquid feeding system to stop the sample when a predetermined second waiting time, which is set independently of the first waiting time, has passed from the time when the passage of the sample through the detection region is detected by the detection system.

Still another embodiment of the present invention also relates to a method for controlling a reaction processor that comprises: a reaction processing vessel in which a channel where a sample moves is formed; a liquid feeding system that moves and stops the sample in the channel; a temperature control system that provides a first temperature region maintained at a first temperature and a second temperature region maintained at a second temperature lower than the first temperature in the channel; and a detection system that detects the sample passing through a detection region that is set between the first temperature region and the second temperature region of the channel. In this method, given that: when the sample moves from the second temperature region to the first temperature region, the moving speed of the sample in the detection region is denoted as a first moving speed $v_1$, and the distance between an end portion of the sample stopping at a predetermined position in the channel that is closest to the detection region and the center of the detection region is denoted as $X_{01}$; when the sample moves from the first temperature region to the second temperature region, the moving speed of the sample in the detection region is denoted as a second moving speed $v_2$, and the distance between an end portion of the sample stopping at a predetermined position in the channel that is closest to the detection region and the center of the detection region is denoted as $X_{02}$; and when a fixed period of time specific to the reaction processor is denoted as $t_c$, the control unit instructs the liquid feeding system to stop the sample when a first waiting time defined by $t_{d2/1}=X_{01}/v_1-t_c$ has passed when the sample moves from the second temperature region to the first temperature region and when a second waiting time defined by $t_{d2/2}=X_{02}/v_2-t_c$ has passed when the sample moves from the first temperature region to the second temperature region.

Still another embodiment of the present invention also relates to a method for controlling a reaction processor that comprises: a reaction processing vessel in which a channel where a sample moves is formed; a liquid feeding system that moves and stops the sample in the channel; a temperature control system that provides a first temperature region maintained at a first temperature and a second temperature region maintained at a second temperature lower than the first temperature in the channel; and a detection system that detects the sample passing through a detection region that is set between the first temperature region and the second temperature region of the channel. In this method, given that: when the sample moves from the second temperature region to the first temperature region, the moving speed of the sample in the detection region is denoted as a first moving speed $v_1$, and the distance between an end portion of the sample stopping at a predetermined position in the channel that is closest to the detection region and the center of the detection region is denoted as $X_{01}$; when the sample moves from the first temperature region to the second temperature region, the moving speed of the sample in the detection region is denoted as a second moving speed $v_2$, and the distance between an end portion of the sample stopping at a predetermined position in the channel that is closest to the detection region and the center of the detection region is denoted as $X_{02}$; and when a fixed period of time specific to the reaction processor is denoted as $t_c$, and a and R are defined as correction coefficients, the control unit instructs the liquid feeding system to stop the sample when a first waiting time defined by $t_{d2/1}=\alpha*(X_{01}/v_1)-t_c$ has passed when the sample moves from the second temperature region to the first temperature region and when a second waiting time defined by $t_{d2/2}=\beta*(X_{02}/v_2)-t_c$ has passed when the sample moves from the first temperature region to the second temperature region.

An explanation will be given regarding "the passage of the sample through the detection region". Since a sample that is subjected to PCR has a fixed volume, the sample has a predetermined length sectioned by an interface with the air in the channel. When the sample subjected to PCR moves in a certain direction, the sample has a leading end part including a leading interface and a rear end part including a rearmost interface. The expression "the passage of the sample through the detection region" means that the leading end part of the sample enters the detection region and the rear end portion then exits the detection region when the sample is moving in a certain direction.

The expression "the time when the sample has passed through the detection region" means the time when the rear end part of the sample exits the detection region. Further, the expression "the transit time of the sample (through the detection region)" means the time required from the time when the leading end part of the sample enters the detection region until the time the rear end part of the sample exits the detection region and is the time required for the sample having a predetermined length to pass through the detection region.

An explanation will be given now regarding "the position of the sample". In the present specification, etc., when the sample in the channel moves in a direction getting away from the detection region after passing through the detection region or stops after moving in a direction away from the detection region, "the position of the sample" is expressed by the distance X between an interface belonging to the end part of the sample that is closest to the detection region and the center of the detection region.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIGS. 3A and 3B are diagrams for explaining the stopping position of a sample;

DETAILED DESCRIPTION OF THE INVENTION

Figure 1A:
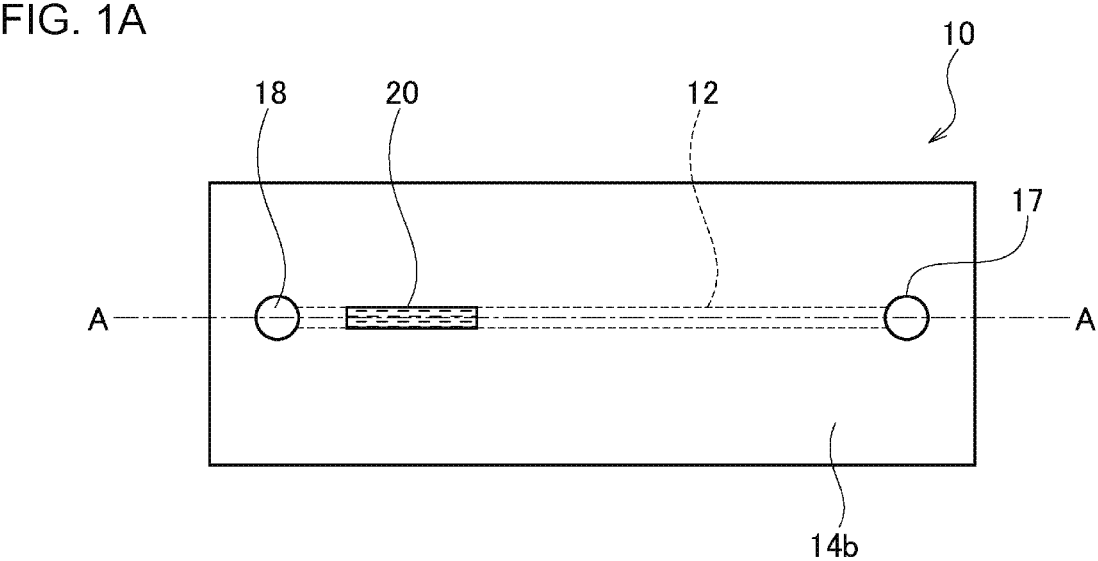
FIGS. 1A and 1B are diagrams for explaining a reaction processing vessel usable in a reaction processor according to an embodiment of the present invention.

An explanation will be given in the following regarding a reaction processor according to an embodiment of the present invention. This reaction processor is a device for performing PCR. The same or equivalent constituting elements, members, and processes illustrated in each drawing shall be denoted by the same reference numerals, and duplicative explanations will be omitted appropriately. Further, the embodiments do not limit the invention and are shown for illustrative purposes, and all the features described in the embodiments and combinations thereof are not necessarily essential to the invention.

Figure 1B:
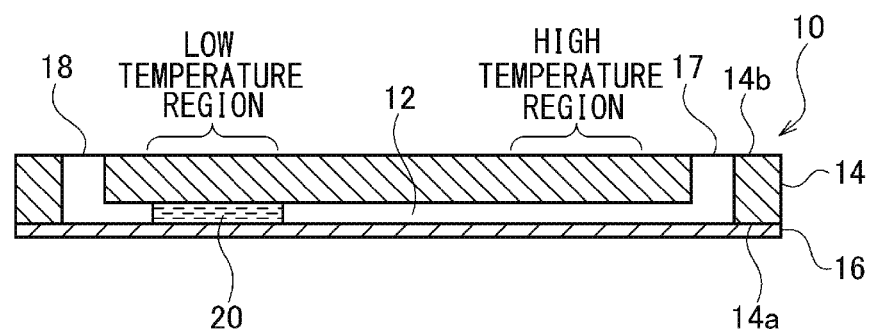

FIGS. 1A and 1B are diagrams for explaining a reaction processing vessel 10 usable in a reaction processor according to an embodiment of the present invention. FIG. 1A is a plan view of the reaction processing vessel 10, and FIG. 1B is a cross-sectional view of the reaction processing vessel 10 shown in FIG. 1A that is sectioned along line A-A.

As shown in FIGS. 1A and 1B, the reaction processing vessel 10 comprises a substrate 14 and a channel sealing film 16.

The substrate 14 is preferably formed of a material that is stable under temperature changes and is resistant to a sample solution that is used. Further, the substrate 14 is preferably formed of a material that has good moldability, a good transparency and barrier property, and a low self-fluorescence property. As such a material, an inorganic material such as glass, silicon (Si), or the like, a resin such as acrylic, polyester, silicone, or the like, and particularly cycloolefin are preferred. An example of the dimensions of the substrate 14 includes a long side of 75 mm, a short side of 25 mm, and a thickness of 4 mm.

A groove-like channel 12 is formed on the lower surface 14a of the substrate 14, and this channel 12 is sealed by the channel sealing film 16. An example of the dimensions of the channel 12 formed on the lower surface 14a of the substrate 14 includes a width of 0.7 mm and a depth of 0.7 mm. A first communication port 17, which communicates with the outside, is formed at the position of one end of the channel 12 in the substrate 14. A second communication port 18 is formed at the position of the other end of the channel 12 in the substrate 14. The pair, the first communication port 17 and the second communication port 18, formed on the respective ends of the channel 12 is formed so as to be exposed on the upper surface 14b of the substrate 14. Such a substrate can be produced by injection molding or cutting work with an NC processing machine or the like.

On the lower surface 14a of the substrate 14, the channel sealing film 16 is attached. In the reaction processing vessel 10 according to the embodiment, most of the channel 12 is formed in the shape of a groove exposed on the lower surface 14a of the substrate 14. This is for allowing for easy molding by injection molding using a metal mold or the like. In order to seal this groove so as to make use of the groove as a channel, the channel sealing film 16 is attached on the lower surface 14a of the substrate 14.

The channel sealing film 16 may be sticky on one of the main surfaces thereof or may have a functional layer that exhibits stickiness or adhesiveness through pressing, energy irradiation with ultraviolet rays or the like, heating, etc., formed on one of the main surfaces. Thus, the channel sealing film 16 has a function of being easily able to become integral with the lower surface 14a of the substrate 14 while being in close contact with the lower surface 14a. The channel sealing film 16 is desirably formed of a material, including an adhesive, that has a low self-fluorescence property. In this respect, a transparent film made of a resin such as cycloolefin, polyester, polypropylene, polyethylene or acrylic is suitable but is not limited thereto. Further, the channel sealing film 16 may be formed of a plate-like glass or resin. Since rigidity can be expected in this case, the channel sealing film 16 is useful for preventing warpage and deformation of the reaction processing vessel 10.

The channel 12 is provided with a reaction region where the control of temperatures of a plurality of levels is possible by a reaction processor described later. A thermal cycle can be applied to a sample by moving the sample such that the sample continuously reciprocates in the reaction region where the temperatures of a plurality of levels are maintained. The channel 12 shown in FIGS. 1A and 1B is formed in a linear shape. When the reaction processing vessel 10 is mounted on a reaction processor described later, the right side of the channel 12 in the figures is expected to become a reaction region of a relatively high temperature (about 95° C.) (hereinafter referred to as "high temperature region"), and the left side of the channel 12 is expected to become a region of a lower temperature (about 55° C.) (hereinafter referred to as "low temperature region").

In FIGS. 1A and 1B, the reaction region of the channel 12 is formed in a linear shape. However, the form of the reaction region is not limited thereto, and the reaction region may be formed in a so-called serpiginous shape where a turn is continuously made by combining curved portions and straight portions. In this case, the effective area of a heater or the like constituting a temperature control means described later can be effectively used, and there are advantages that temperature variance in the reaction region is easily reduced and that the substantial size of the reaction processing vessel can be reduced, allowing the reaction processor to be made small.

FIGS. 1A and 1B show a state where a sample 20 is introduced into the channel of the reaction processing vessel 10. The sample 20 is introduced into the channel 12 through either one of the first communication port 17 and the second communication port 18. The method for the introduction is not limited to this. Alternatively, for example, an appropriate amount of the sample may be directly introduced through the communication port using a pipette, a dropper, a syringe, or the like. Alternatively, a method of introduction may be used that is performed while preventing contamination via a cone-shaped needle chip, in which a filter made of porous PTFE or polyethylene is incorporated. In general, many types of such needle chips are sold and can be obtained easily, and the needle chips can be used while being attached to the tip of a pipette, a dropper, a syringe, or the like. Furthermore, the sample may be moved to a predetermined position in the channel by discharging and introducing the sample by a pipette, a dropper, a syringe, or the like and then further pushing the sample through pressurization.

The sample 20 includes, for example, those obtained by adding a fluorescent probe, a thermostable enzyme and four types of deoxyribonucleoside triphosphates (dATP, dCTP, dGTP, dTTP) as PCR reagents to a mixture containing one or more types of DNA. Further, a primer that specifically reacts to DNA subjected to a reaction process is mixed. Commercially available real-time PCR reagent kits and the like can be also used.

Figure 2:
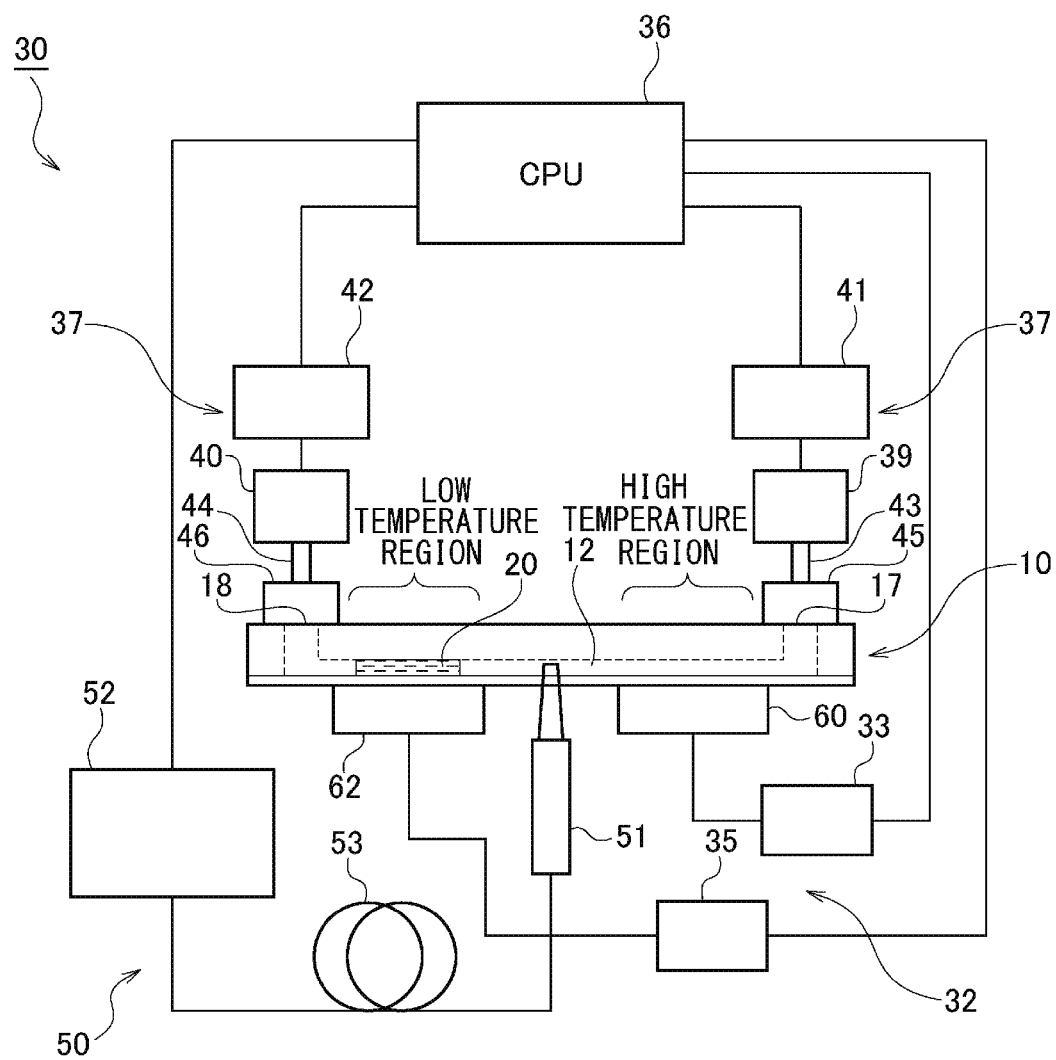
FIG. 2 is a schematic diagram for explaining the reaction processor according to the embodiment of the present invention.

FIG. 2 is a schematic diagram for explaining a reaction processor 30 according to the embodiment of the present invention.

The reaction processor 30 according to the embodiment is provided with a reaction processing vessel placing portion (not shown) on which the reaction processing vessel 10 is placed, a temperature control system 32, and a CPU 36. As shown in FIG. 2, relative to the reaction processing vessel 10 placed on the reaction processing vessel placing portion, the temperature control system 32 is configured so as to be able to accurately maintain and control the temperature of the right side region of the channel 12 of the reaction processing vessel 10 in the figure to be about 95° C. (high temperature range) and the temperature of the left side region thereof in the figure to be about 55° C. (low temperature range).

The temperature control system 32 is for maintaining the temperature of each temperature region of a thermal cycle region and is specifically provided with a high temperature heater 60 for heating the high temperature region of the channel 12, a low temperature heater 62 for heating the low temperature region of the channel 12, a temperature sensor (not shown) such as, for example, a thermocouple or the like for measuring the actual temperature of each temperature region, a high temperature heater driver 33 for controlling the temperature of the high temperature heater 60, and a low temperature heater driver 35 for controlling the temperature of the low temperature heater 62. Information on the actual temperature measured by the temperature sensor is sent to the CPU 36. Based on the information on the actual temperature of each temperature region, the CPU 36 controls each heater driver such that the temperature of each heater becomes a predetermined temperature. Each heater may be, for example, a resistance heating element, a Peltier element, or the like. The temperature control system 32 may be further provided with other components for improving the temperature controllability of each temperature region.

The reaction processor 30 according to the embodiment is further provided with a liquid feeding system 37 for moving the sample 20 inside the channel of the reaction processing vessel 10. The liquid feeding system 37 is provided with a first pump 39, a second pump 40, a first pump driver 41 for driving the first pump 39, a second pump driver 42 for driving the second pump 40, a first tube 43, and a second tube 44.

One end of the first tube 43 is connected to the first communication port 17 of the reaction processing vessel 10. A packing material 45 or a seal for securing airtightness is preferably arranged at the junction of the first communication port 17 and the end of the first tube 43. The other end of the first tube 43 is connected to the output of the first pump 39. In the same way, one end of the second tube 44 is connected to the second communication port 18 of the reaction processing vessel 10. A packing material 46 or a seal for securing airtightness is preferably arranged at the junction of the second communication port 18 and the end of the second tube 44. The other end of the second tube 44 is connected to the output of the second pump 40.

The first pump 39 and the second pump 40 may be, for example, micro blower pumps each comprising a diaphragm pump. As the first pump 39 and the second pump 40, for example, micro blower pumps (MZB1001 T02 model) manufactured by Murata Manufacturing Co., Ltd., or the like can be used. While these micro blower pumps can increase the pressure on a secondary side to be higher than a primary side during operation, the pressure on the primary side and the pressure on the secondary side become equal at the moment when the pumps are stopped or when the pumps are stopped.

The CPU 36 controls the air supply and pressurization from the first pump 39 and the second pump 40 via the first pump driver 41 and the second pump driver 42. The air supply and pressurization from the first pump 39 and the second pump 40 act on the sample 20 inside the channel through the first communication port 17 and the second communication port 18 and become a propulsive force to move the sample 20. More specifically, by alternately operating the first pump 39 and the second pump 40, the pressure applied to either end surface of the sample 20 becomes larger than the pressure applied to the other end, and a propulsive force relating to the movement of the sample 20 can thus be obtained. By alternately operating the first pump 39 and the second pump 40, the sample 20 can be moved in a reciprocating manner in the channel so as to pass through each temperature region of the channel 12 of the reaction processing vessel 10. As a result, a thermal cycle can be applied to the sample 20. More specifically, target DNA in the sample 20 is selectively amplified by repeatedly applying a step of denaturation in the high temperature region and a step of annealing and elongation in the low temperature region. In other words, the high temperature region can be considered to be a denaturation temperature region, and the low temperature region can be considered to be an annealing and elongation temperature region. The time for staying in each temperature region can be appropriately set by changing the time during which the sample 20 stops at a predetermined position in each temperature region.

The reaction processor 30 according to the embodiment is further provided with a fluorescence detector 50. As described above, a predetermined fluorescent probe is added to the sample 20. Since the intensity of a fluorescence signal emitted from the sample 20 increases as the amplification of the DNA proceeds, the intensity value of the fluorescence signal can be used as an index serving as a decision material for the progress of the PCR or the termination of the reaction.

As the fluorescence detector 50, an optical fiber-type fluorescence detector FLE-510 manufactured by Nippon Sheet Glass Co., Ltd., can be used, which is a very compact optical system that allows for rapid measurement and the detection of fluorescence regardless of whether the place is a lighted place or a dark place. This optical fiber-type fluorescence detector allows the wavelength characteristic of the excitation light/fluorescence to be tuned such that the wavelength characteristic is suitable for the characteristic of fluorescence emitted from the sample 20 and thus allows an optimum optical and detection system for a sample having various characteristics to be provided. Further, the optical fiber-type fluorescence detector is suitable for detecting fluorescence from a sample existing in a small or narrow region such as a channel because of the small diameter of a ray of light brought by the optical fiber-type fluorescence detector.

The optical fiber-type fluorescence detector 50 is provided with an optical head 51, a fluorescence detector driver 52, and an optical fiber 53 connecting the optical head 51 and the fluorescence detector driver 52. The fluorescence detector driver 52 includes a light source for excitation light (LED, a laser, or a light source adjusted to emit other specific wavelengths), an optical fiber-type multiplexer/demultiplexer and a photoelectric conversion device (PD, APD, or a light detector such as a photomultiplier) (neither of which is shown), and the like and formed of a driver or the like for controlling these. The optical head 51 is formed of an optical system such as a lens and has a function of directionally irradiating the sample with excitation light and collecting fluorescence emitted from the sample. The collected fluorescence is separated from the excitation light by the optical fiber-type multiplexer/demultiplexer inside the fluorescence detector driver 52 through the optical fiber 53 and converted into an electric signal by the photoelectric conversion element.

In the reaction processor 30 according to the present embodiment, the optical head 51 is arranged such that fluorescence from the sample 20 in the channel connecting the high temperature region and the low temperature region can be detected. Since the reaction progresses while the sample 20 is repeatedly moved in a reciprocating manner in the channel such that predetermined DNA contained in the sample 20 is amplified, by monitoring a change in the amount of detected fluorescence, the progress of the DNA amplification can be learned in real time. Further, in the reaction processor 30 according to the embodiment, an output value from the fluorescence detector 50 is utilized for controlling the movement of the sample 20, as described later. The fluorescence detector is not limited to an optical fiber-type fluorescence detector as long as the fluorescence detector exhibits the function of detecting fluorescence from a sample.

FIGS. 3A and 3B are diagrams for explaining the stopping position of a sample. As described above, in the reaction processor 30 according to the embodiment, in order to apply a thermal cycle to the sample 20 by moving the sample in a reciprocating manner in the channel, a plurality of temperature regions (i.e., the high temperature region and the lower temperature region) each maintained at a different temperature are set on the channel 12. In order to properly apply a thermal cycle to the sample 20, it is necessary for the sample 20 to stop accurately in each temperature region. Variations in the stopping position may prevent reactions from occurring, cause reactions to vary according to the location of the sample, and cause reactions such as amplification of DNA to be inaccurate, which may lead to erroneous judgment by workers and/or those engaged in the work.

As shown in FIG. 3B, the channel 12 is provided with a connection region for connecting the high temperature region and the low temperature region. The optical head 51 of the fluorescence detector 50 is provided so as to detect fluorescence from the sample 20 passing through a partial region 65 (referred to as "fluorescence detection region 65") in this connection region. The fluorescence detector 50 detects a fluorescence signal from the sample 20 in the fluorescence detection region 65 and transmits the signal to the CPU 36 every 0.01 second. The CPU 36 receives the fluorescence signal, performs arithmetic processing such as smoothing of the fluorescence signal value and averaging such as moving average, comparison with a predetermined threshold value (hereinafter sometimes collectively referred to as "evaluation and the like"), and the like, and provides a stop or operation signal to the liquid feeding system 37 based on the result thereof.

In FIG. 3A and FIG. 3B, the fluorescence detection region 65 is arranged close to the middle part between the high temperature region and the low temperature region; however, this is non-limiting. For example, the arrangement thereof may be biased toward the high temperature region side or the low temperature region side. Since the output of the low temperature heater 62 arranged in the low temperature region may be lower than that of the high temperature heater 60 arranged in the high temperature region, it is possible to use heater parts that are accordingly small or thin, and in that case, the optical head 51 can be also arranged while being biased toward the low temperature region.

A case is now taken into consideration where the sample 20 is stopped at a position spaced apart from the center of the fluorescence detection region 65 by a predetermined distance. A distance X corresponding to the position (target stop position) of the sample 20 to be stopped is represented by the distance $X_0$. The distance $X_0$ is the distance between an interface belonging to the end portion of the sample 20 that is closest to the fluorescence detection region 65 and the center of the fluorescence detection region 65 when the sample 20 stops at the target stop position after passing through the fluorescence detection region 65. When the sample 20 is present at the position indicated by the distance $X_0$, the sample 20 is most appropriately heated and maintained at a predetermined temperature, and this position is determined based on the range and position of the temperature region of the processor and the configuration of the reaction processing vessel 10.

As described above, in the case, e.g., where the position of the fluorescence detection region 65 is biased toward either the high temperature region or the low temperature region, the distance corresponding to the target stop position on the high temperature region side and the distance corresponding to the target stop position on the low temperature region side are different. Hereinafter, when considering a general target stop position, the target stop position is described as $X_0$. However, it is to be noted that, as described above, the distance corresponding to the target stop position on the high temperature region side and the distance corresponding to the target stop position on the low temperature region side do not need to be the same. In the present specification, the distance corresponding to the target stop position on the high temperature region side is represented $X_{01}$, and the distance corresponding to the target stop position on the low temperature region side is represented by $X_{02}$.

The flow for stopping the sample 20 is shown below.
(1) The sample 20 passes through the fluorescence detection region 65 (the fluorescence detector 50 transmits a fluorescence signal to the CPU 36).
(2) The CPU 36 detects the passage of the sample 20 based on the fluorescence signal from the fluorescence detector 50.
(3) The CPU 36 transmits a stop signal for the first pump 39 to the first pump driver 41 or transmits a stop signal for the second pump 40 to the second pump driver 42.
(4) The first pump 39 or the second pump 40 stops.
(5) Sample 20 stops.

Using a chart diagram of FIG. 4, an explanation will be given of a mode in which the sample 20 moving in the channel 12 at the speed v (mm/s) stops at the target stop position corresponding to the distance $X_0$ (mm) after a predetermined period of time after passing the fluorescence detection region 65. The chart diagram of FIG. 4 schematically shows a mode generally occurring in the case of a control system as described above. In this explanation, there is no distinction between the high temperature region and the low temperature region on the channel 12, and the channel 12 having no temperature distribution within the movement range of the sample 20 is considered.

Figure 4A:
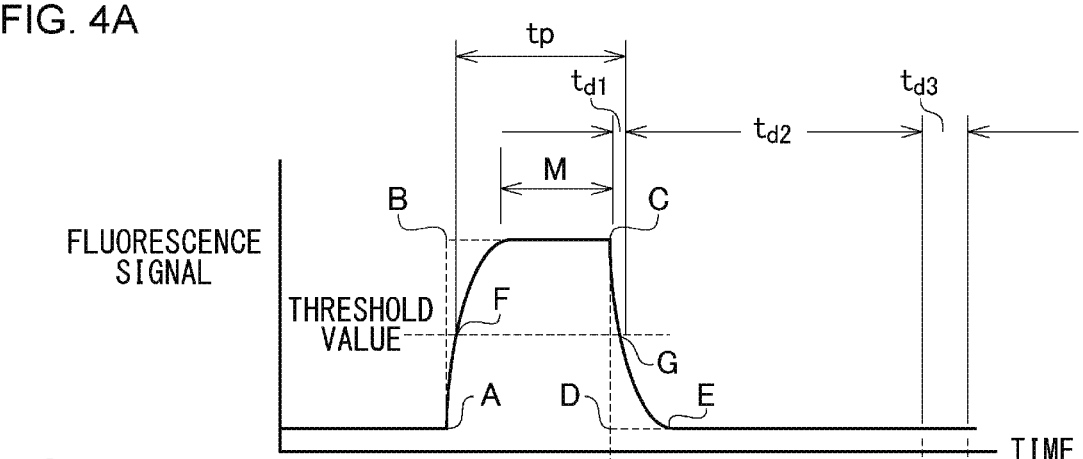
FIGS. 4A, 4B and 4C are a fluorescence signal chart diagram, a sample position chart diagram, a sample speed chart diagram, respectively, for a period from when a sample passes through a fluorescence detection region until the sample stops after a waiting time is set.
Figure 4B:
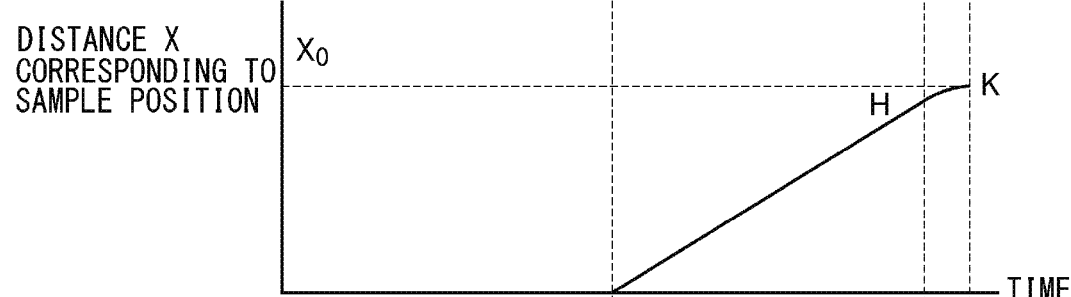
Figure 4C:
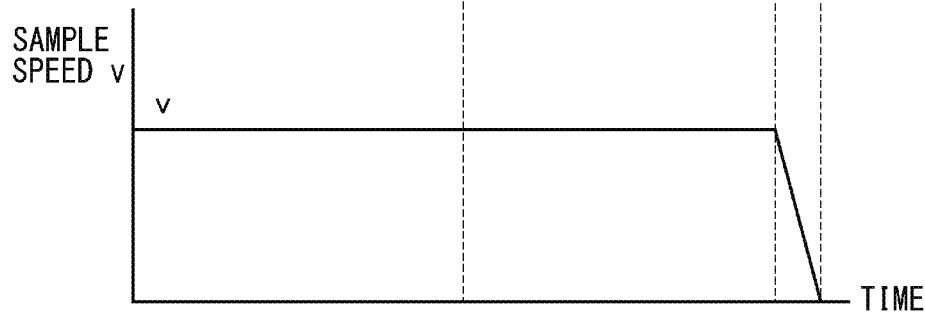

FIG. 4A schematically shows a mode of a fluorescence signal when the sample 20 passes through the fluorescence detection region 65 (fluorescence signal chart). FIG. 4B shows changes in the distance X corresponding to the position of the sample 20 in a time series manner (sample position chart). FIG. 4C shows changes in the moving speed of the sample 20 in a time series manner (sample speed chart). The substantial area of the fluorescence detection region 65 is assumed to be very small here. This is because the area of the fluorescence detection region 65 corresponds to the area of irradiation with excitation light collected by an objective lens and is therefore 1 mm or less in diameter, which is much smaller than the length of the sample 20 and the distance $X_0$.

FIG. 4A shows, using a solid line, a fluorescence signal obtained by performing an operation such as moving averaging processing of the CPU 36 on a fluorescence signal detected by the fluorescence detector 50 when the sample 20 having a certain length in the channel 12 passes through the fluorescence detection region 65. In an ideal case where there is no time lag in the fluorescence detector 50, the CPU 36, or the like, a substantially rectangular fluorescent signal as drawn by a dotted line, that is, a fluorescent signal following the dotted line from a point A to a point B to a point C to a point D and then converging to the baseline again in FIG. 4A should be detected. However, as described above, since the CPU 36 receives a fluorescence signal every 0.01 second from the fluorescence detector 50 and performs the evaluation and the like on the signal, in reality, a fluorescence signal drawn by the solid line accompanied with a delay corresponding to the time required for the evaluation and the like is detected, that is, a fluorescence signal that shows a peak (corresponding to a region M) lagging behind the dotted line while following the solid line from the point A in FIG. 4A and that then becomes reduced and converges to the baseline toward the point E lagging behind the dotted line while following the solid line is detected.

In the present embodiment, based on the fluorescence signal according to the mode as shown in FIG. 4A detected by the CPU 36, it is necessary to determine in advance the condition of the fluorescence signal that allows the CPU 36 to recognize that "the sample has passed through the fluorescence detection region" (hereinafter, referred to as "criterion for sample passage"). Although the criterion for sample passage is not limited to this, in the present embodiment, given that the half value (50% value) between the baseline and the peak value of a fluorescence signal is set as a threshold value, that a point at which a fluorescent signal obtained every 0.01 second through the operation such as moving averaging processing becomes equal to or higher than this threshold value at the time of the rising of the fluorescent signal is defined as point F, and that a point at which the fluorescent signal becomes equal to or lower than the threshold value at the time of the falling of the fluorescent signal is defined as point G, the time corresponding to the point F and the time corresponding to the point G in the fluorescence signal chart of FIG. 4A correspond to the time when the CPU 36 has detected that the leading end part of the sample has entered the fluorescence detection region and the time when the CPU 36 has detected that the rear end part of the sample has exited the fluorescence detection region, respectively. Further, $t_{d1}$, which is the difference between the time corresponding to the point C and the time corresponding to the point G, can be considered as a delay time from the time when the sample 20 actually passed through the fluorescence detection region 65 until the time when the CPU 36 detects that the sample 20 has passed through the fluorescence detection region 65. This is also the time required for (1) through (2) described in the above flow and is constant even if the moving speed of the sample or the like is changed due to the control system or those that are specific to the method of the evaluation and the like by the CPU 36 described above.

Further, in the fluorescence signal chart of FIG. 4A, it is to be noted that the time $t_p$ is the time required for the sample 20 having a certain length in the channel 12 to pass through the fluorescence detection region 65. When the moving speed v of the sample 20 changes, for example, when v increases, $t_p$ decreases, and a substantially rectangular pulse-like chart of the fluorescence signal chart changes to a form where the width thereof is reduced. When v decreases, the chart appears as a chart of the fluorescent signal whose width is increased, on the contrary.

In the fluorescence signal chart of FIG. 4A, a stop signal is transmitted $t_{d2}$ seconds after the time corresponding to the point G to the liquid feeding system 37. The time from when the pump driver of the liquid feeding system 37 receives the stop signal until the pump stops can be ignored. The evaluation and the like of the signal that has been received are not necessary, and the pump that is used is not an inertia-driven type pump. The time $t_{d2}$ is the time required for (2) through (3) described in the above flow and is the time to be determined for controlling the processor, i.e., for the control for stopping the sample 20 at a predetermined position instead of being a delay time the processor inevitably has.

In the sample position chart of FIG. 4B and the sample speed chart of FIG. 4C, a delay time $t_{d3}$ occurs from when the pump (the first pump 39 or the second pump 40) stops at the time corresponding to the point H until when the sample stops at the time corresponding to the point K. This is because, in general, it is hard to consider that a sample or the like having substantial mass that is moving at a predetermined speed while obtaining a propulsive force from the outside (exceeding the resistance such as a frictional force) stops simultaneously when the propulsive force is cut off. $t_{d3}$ is the time required for (3) through (5) described in the above flow.

In a reciprocating channel type PCR device provided with the control system according to the present embodiment, at the time corresponding to the point G in FIG. 4A, the CPU 36 and the like can detect that the sample 20 has passed through the fluorescence detection region 65. Therefore, by transmitting a stop signal to the pump driver (41 or 42) of the liquid feeding system 37 $t_{d2}$ seconds after this time, it is possible to stop the sample 20 at the target stop position corresponding to the distance $X_0$. Thus, a challenge is to specifically determine this time period $t_{d2}$. Since this time period $t_{d2}$ indicates how long the CPU needs to wait for the stop signal to be transmitted, the time is referred to as "waiting time".

From the chart diagrams of FIGS. 4B and 4C, since the moving speed times the time equals the distance, the following equation (1) is established.

$$v^* t_{d1} + V^* t_{d2} + v^* t_{d3}/2 = X_0 \tag{1}$$

When this equation (1) is transformed, the following equation (2) is obtained.

$$t_{d2} = X_0/v - (t_{d1} + t_{d3}/2) \tag{2}$$

In this equation (2), $(t_{d1} + t_{d3}/2)$ is an inherent time dependent on the processor, sample, etc., and when this is defined as "delay time" tc, equation (3) is obtained.

$$t_{d2} = X_0/v - t_c \tag{3}$$

The meaning of this equation (3) is now considered. In general, in order to stop an object that is moving on an observation point at a moving speed v at a position away from the observation point by a distance $X_0$, the object needs to be stopped a time period of $X_0/v$ after the object passes through the observation point. However, in the present embodiment, as can be understood from FIG. 4A, it can be considered that the sum of the time required for the evaluation and the like by the CPU 36 and the transmission of the stop signal to the liquid feeding system 37 and furthermore the time required for the sample 20 to stop completely after the pump 39 or 40 stops, or the like is the so-called delay time and appears as $t_c$ in the equation (3).

Before the waiting time $t_{d2}$ is specifically obtained, a detailed explanation will be made regarding how to obtain the moving speed v of the sample 20 based on fluorescence signal data that has been actually obtained. The sample 20 has a finite length L (for example, around 40 mm) inside the channel. Therefore, if the time $t_p$ the sample 20 takes to pass through the fluorescence detection region 65 is known, it is possible to calculate the moving speed v of the sample 20 using $v = L/t_p$.

Figure 5:
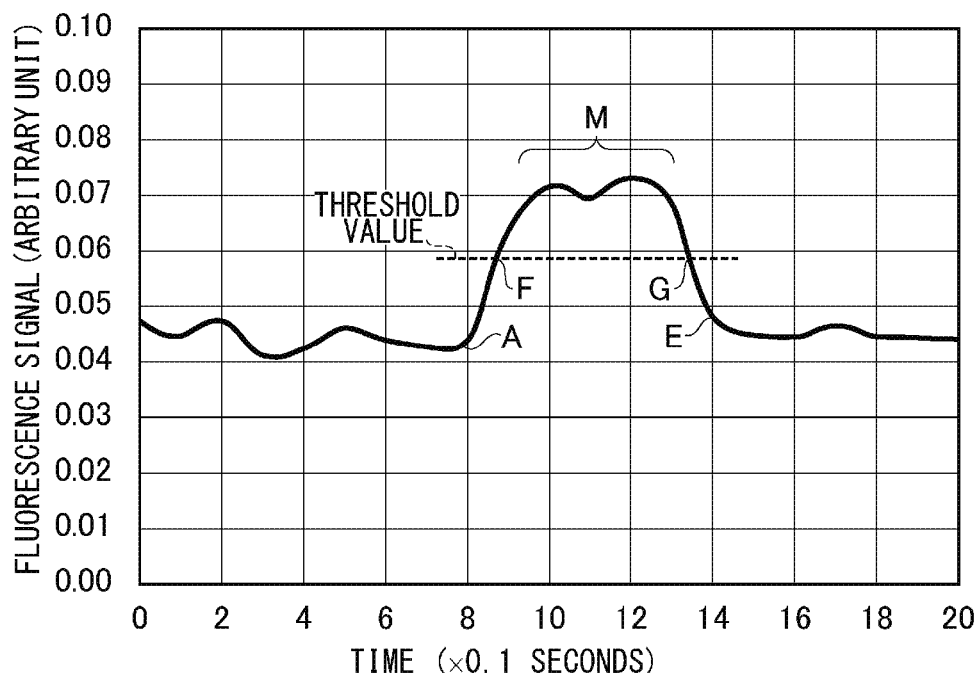
FIG. 5 is a diagram showing changes in a fluorescence signal.

FIG. 5 shows changes in a fluorescence signal detected by the fluorescence detector 50 and obtained as a result of an operation such as moving averaging processing by the CPU 36. For the symbols in the figure, the same symbols as those in FIG. 4A showing the relationship between the time and the fluorescence signal are used based on the correspondence relationship. The fluorescence signal graph shown in FIG. 5 is for the beginning of the reaction. In FIG. 5, the horizontal axis shows time while setting the time before the sample 20 enters the fluorescence detection region 65 and when the detection of a fluorescence signal is started to be 0, and the vertical axis shows the intensity (in a case where a photoelectric conversion element such as APD is used as a fluorescence detection device, the direct output of the fluorescence signal is expressed using voltage) of the fluorescence signal output from the fluorescence detector driver 52. As shown in FIG. 5, when the sample 20 passes through the fluorescence detection region 65, the relationship between the time and the fluorescence signal that is detected is such that the fluorescence signal increases from zero or a baseline as the sample 20 enters the fluorescence detection region 65 and the fluorescence signal drops to zero or the baseline again as the sample 20 exits the fluorescence detection region 65.

In FIG. 5, as a graph showing the change of the fluorescence signal at the time of sample passage, a graph of a substantially rectangular shape (having a plateau-like peak) is illustrated. However, in addition to this, for example, in the case where air bubbles are mixed in the sample 20 or where there is reaction variation in the sample 20, there is a possibility that variation of various sizes appear in the flatness of the plateau-like peak in the region M such as the occurrence of a steep depression or kink. Further, when the length of the sample 20 in the channel is small or when the moving speed of the sample 20 is high, there is a possibility that a form may appear where the flat part of the plateau-like peak in the region M becomes narrow. Further, it is considered that a part that is rising from the point A to the region M and a part that is falling from the region M to the point E have a slanting form resulting from having a fixed time constant due to the time spent for the evaluation and the like by the CPU 36, as explained in FIG. 4A. In the present embodiment, in order to obtain a stable fluorescent signal, the previously-described signal processing such as the evaluation and the like by the CPU 36 is performed. However, this is an example of electrical processing or evaluation, and the embodiment is not limited to the presence or absence of such processing and the evaluation method.

Based on the graph shown in FIG. 5, transit time $t_p$ of the sample 20 passing through the fluorescence detection region 65 is obtained. Since the transit time $t_p$ is a difference in time, the transit time is not affected by the delay time of the processor. As the criterion for sample passage in the present embodiment, 50% of the difference between the baseline and the peak value is set as a threshold value, the time corresponding to a point F in FIG. 5 is set as entry time of (the leading end part of) the sample 20, the time corresponding to a point G is set as exit time of (the rear end part of) the sample 20, and a difference between the time corresponding to the point F and the time corresponding to the point G is set as the transit time $t_p$ of the sample 20. Those skilled in the art can arbitrarily and freely set the percentage of the difference between the peak value of the fluorescence signal and the baseline for the threshold value. Based on the known length L of the sample 20 and the transit time t, of the sample 20, the CPU 36 can calculate the moving speed v of the sample 20 using $v=L/t_p$.

The sample 20 generates fluorescence from the beginning of the reaction; however, it is not necessary to continue using the same threshold value based on the fluorescence signal graph for the beginning of the reaction and continue obtaining the transit time $t_p$ from the beginning of the reaction until the end of the reaction. By applying a thermal cycle to the sample 20, a predetermined DNA or the like is amplified, and thus the intensity of fluorescence from the sample 20 and the fluorescence signal increase inevitably. Thus, the threshold value may be changed according to the progress of the reaction of the sample 20 (i.e., the threshold value may be increased with an increase in the difference between the baseline and the peak value in the fluorescence signal graph).

Figure 6:
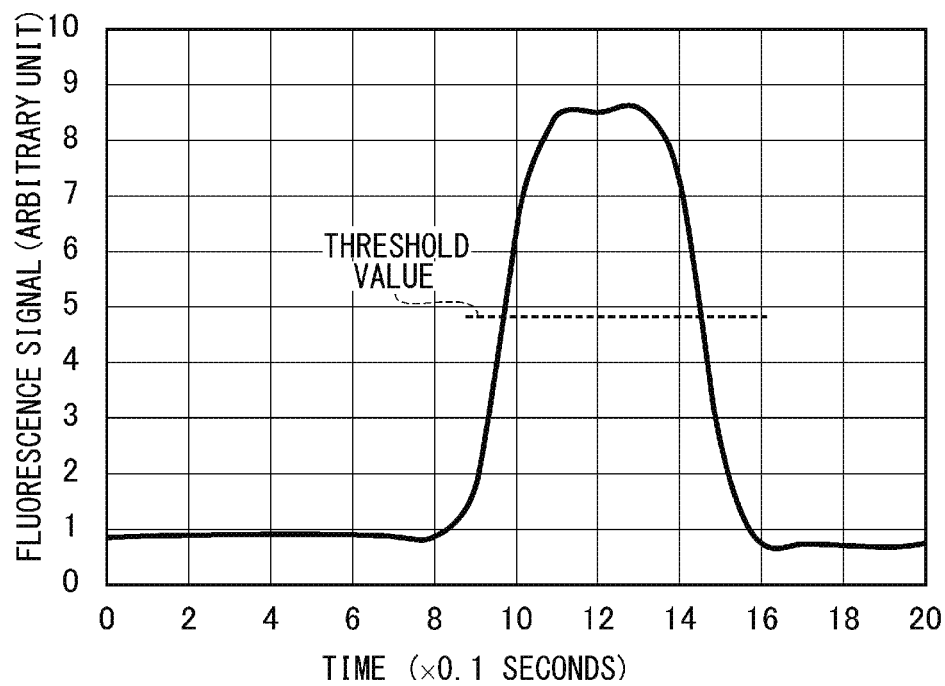
FIG. 6 is a diagram showing changes in a fluorescence signal at a point in time when a reaction has proceeded to a certain extent.

FIG. 6 shows changes in a fluorescence signal at a point in time when the reaction has proceeded to a certain extent. In general, as the reaction progresses, the fluorescence signal emitted from the sample 20 becomes stronger such that the peak obtained at a point in time when the reaction has proceeded to a certain extent can become 7 to 10 times or even higher than the peak of the fluorescence signal graph for the beginning of the reaction (see FIG. 5). A threshold value set for the 50% line for the difference between the peak value and the baseline at the beginning of the reaction becomes lower than the baseline in the fluorescence signal graph obtained at a point in time when the reaction has proceeded to a certain extent or corresponds to the lower slopes of the peak shape such that the transit time $t_p$ may not be able to be calculated based on the threshold value or the transit time $t_p$ may be determined to have become longer. By changing the threshold value according to the progress of the reaction of the sample 20, it is possible to appropriately obtain the moving speed v of the sample 20 while avoiding such a situation.

The threshold value that serves as the basis for the criterion for the passage of the sample 20 and for the entry and/or exit of the sample 20 is not limited to being determined directly based on a fluorescence signal such as those described above. For example, the criterion for the passage of the sample 20 may be determined based on the change of the fluorescence signal, and the nth order differential coefficient of the fluorescence signal, for example, the first order differential coefficient of the fluorescence signal (corresponding to the change rate of the fluorescence signal) may be calculated so as to determine the time for the entry or exit of the sample 20 by this differential coefficient exceeding a certain threshold value in an increased manner or decreased manner and determine the transit time of the sample 20 based on the difference thereof. Further, in this case, the criterion for the passage of the sample 20 is determined based on the nth order differential coefficient of the fluorescent signal. Therefore, it is also possible to determine that the sample 20 has passed through, for example, when there is a predetermined difference in the rate of change (first order differential coefficient) of the fluorescence signal at a certain point in time compared to the rate of change at a point in time before the certain point in time and to set the level of the difference as the threshold value. Since this can be also compared with the rate of change of the fluorescence signal at an immediately preceding point in time, the entry and exit of the sample 20 into and out of the fluorescence detection region can be detected relatively fast.

Figure 7A:
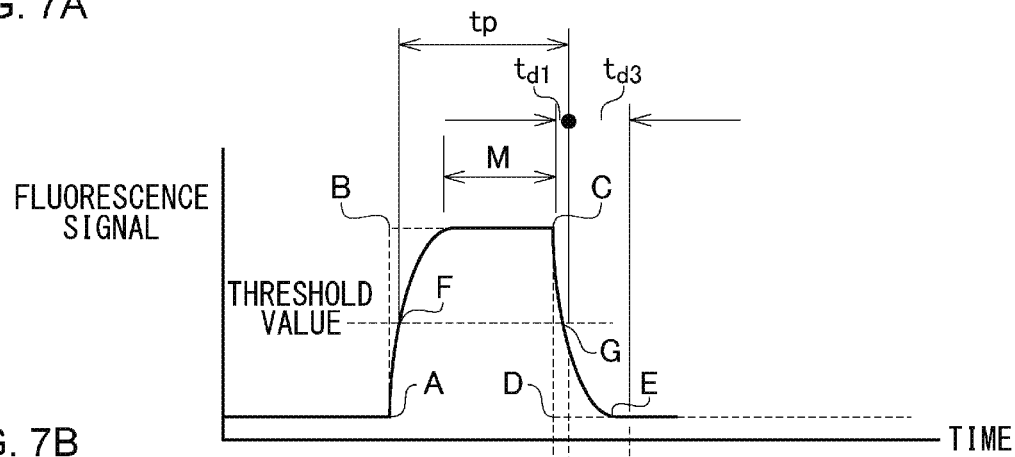
FIGS. 7A, 7B and 7C are a fluorescence signal chart diagram, a sample position chart diagram, a sample speed chart diagram, respectively, for a period from when a sample passes through a fluorescence detection region until the sample stops while having zero waiting time.
Figure 7B:
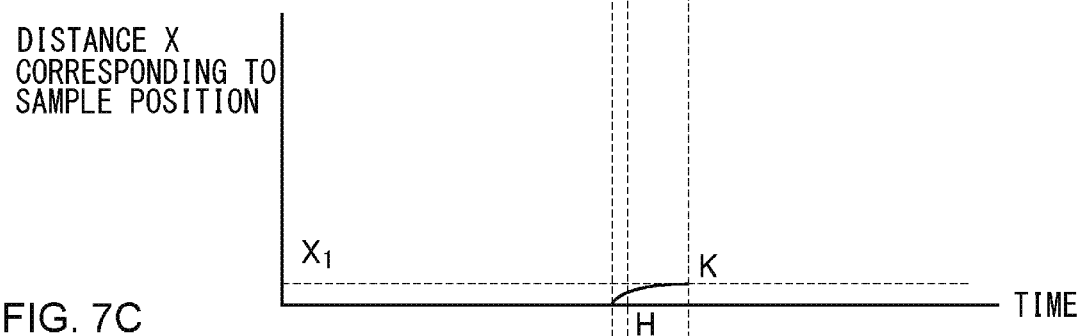
Figure 7C:
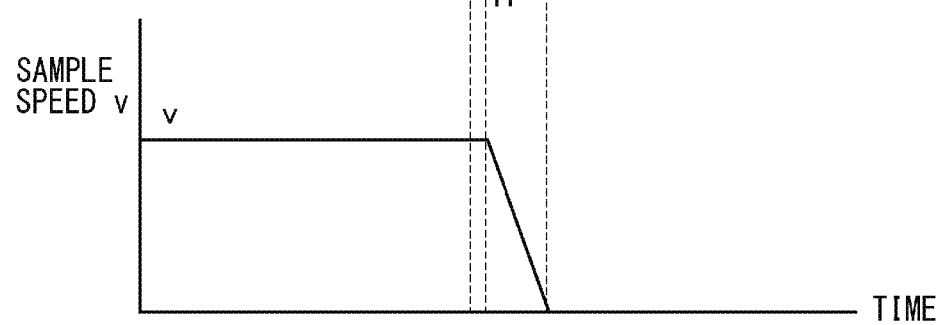

Next, in order to obtain the waiting time $t_{d2}$, $t_c$, that is, the time $t_{d1}$ and the time $t_{d3}$ are studied. First, a system is studied that transmits a stop signal to the liquid feeding system 37 so as to stop the sample 20 by stopping the first pump 39 or the second pump 40 of the liquid feeding system 37 when the waiting time $t_{d2}$ is zero, that is, at the same time the CPU 36 detects the passage of the sample 20 through the fluorescence detection region 65. Chart diagrams obtained at this time are shown in FIGS. 7A to 7C. In the same way as in FIGS. 4A to 4C, FIG. 7A shows a fluorescence signal chart, FIG. 7B shows a sample position chart, and FIG. 7C shows a sample speed chart. For the symbols and the like in the figures, the same symbols and the like as those used in FIGS. 4A to 4C are used. Since the waiting time $t_{d2}$ is zero, a time corresponding to a point G and a time corresponding to a point H are simultaneous with each other. Therefore, when the distance corresponding to the stop position of the sample 20 is denoted as $X_1$ and the moving speed of the sample 20 is denoted as v, the following equation (4) is established based on the charts of FIGS. 7B and 7C.

$$v^*t_{d1}+v^*t_{d3}/2=X_1 \qquad (4)$$

When this equation (4) is transformed, the following equation (5) is obtained.

$$t_{d1}+t_{d3}/2=X_1/v \qquad (5)$$

At this time, it is to be noted that the time $t_{d1}$ and the time $t_{d3}$ are the same as those of the above equation (2). This is because the time $t_{d1}$ and the time $t_{d3}$ are values unique to the processor irrespective of the value of the waiting time $t_{d2}$.

The inventors of the present invention used a voltage (pump voltage E) applied to a pump that can change the moving speed v of the sample 20 as a parameter and obtained the distance $X_1$, which corresponds to the position where the sample 20 actually stopped, the transit time $t_p$, the moving speed v, $X_1/v$ through an experiment or calculation. The results are shown in Table 1.

TABLE 1

| | pump voltage E (V) | | | | | | |
|---|---|---|---|---|---|---|---|
| | 14 | 13.4 | 13 | 12.2 | 11.8 | 11.5 | 11 |
| distance $X_1$ (mm) | 28.0 | 24.2 | 20.5 | 16.7 | 12.6 | 10.7 | 18.1 |
| transit time $t_p$ (s) | 0.30 | 0.33 | 0.39 | 0.50 | 0.64 | 0.70 | 0.97 |
| moving speed v (mm/s) | 133.3 | 121.2 | 102.6 | 80.0 | 62.5 | 57.1 | 41.2 |
| $X_1/v$ (s) | 0.21 | 0.20 | 0.20 | 0.21 | 0.20 | 0.19 | 0.20 |

The sample 20 emitted sufficiently high fluorescence, the volume of the sample 20 was accurately adjusted so that the length L in the channel was 40 mm in any experiment, and the temperature of sample 20 was constantly kept at 40° C. so as to prevent the reaction from occurring. The distance $X_1$ was obtained by measuring the distance from the center of the fluorescence detection region 65 using a digital caliper. Regarding the method of the measurement, measurement under a microscope equipped with a reticle and measurement on a screen that uses a magnified monitor are also possible, but not limited thereto. As described above, the transit time $t_p$ of the sample 20 was obtained, and a stop signal was transmitted to the first pump driver 41 and the second pump driver 42 at the same time the CPU 36 recognized that the sample 20 exited. The moving speed v of the sample 20 was obtained using $v=L/t_p$. For the data in Table 1, an average value for 10 trials was employed for each pump voltage E.

As can be seen from the results in Table 1, $X_1/v$ was 0.19 to 0.21 seconds (about 0.2 seconds on average) even when the moving speed v of the sample 20 was changed by changing the pump voltage E. Since $X_1/v=t_{d1}+t_{d3}/2=t_c$, the following equation (6) is obtained, and the waiting time $t_{d2}$ can be specifically obtained.

$$t_{d2}=X_0/v-t_c \quad (6)$$

In the case of the present embodiment, $t_c$ is about 0.2 seconds.

Therefore, even when $t_{d1}$ and $t_{d3}$ cannot be obtained individually, it is possible to obtain the delay time $t_c$ by performing a moving and stopping experiment while having $t_{d2}$ that is set to 0. It is to be noted that the waiting time $t_{d2}$ needs to satisfy $0 \leq t_{d2}$. This is because the CPU 36 cannot transmit a stop signal to a liquid feeding means before detecting the passage of the sample 20 through the fluorescence detecting region 65. Therefore, it is necessary to determine the distance $X_0$ corresponding to the target stop position of the sample 20 and the moving speed v of the sample 20 in consideration of $t_c$ so that $0 \leq t_{d2}$ is satisfied. $t_{d1}$ is the time required for the evaluation and the like and the transmission of the stop signal by the CPU 36 and is constant regardless of the moving speed v.

The inventors of the present invention conducted a verification experiment regarding the validity of the equation (6). In the verification experiment, a sample 20 that emitted fluorescence with sufficient intensity that allowed for the measurement of the transit time $t_p$ and that had a volume such that the length L in the channel was accurately 40 mm was introduced into the channel 12. During the experiment, the temperature of the sample 20 was maintained at 40° C. so that the reaction did not occur. Further, the moving speed v of the sample 20 was changed by changing the pump voltage E. The moving speed v of the sample 20 was calculated using $v=L/t$ after obtaining the transit time $t_p$ of the sample 20 based on the threshold value at 50% of the difference between the peak and the baseline from the fluorescence signal graph obtained for each pump voltage E. After the distance $X_0$ corresponding to the target stop position of the sample 20 was set to 30 mm and $t_c$ was set to 0.2 seconds, the waiting time $t_{d2}$ was set based on the above study result, and the distance $X_1$ corresponding to the position where the sample 20 actually stopped was measured. The measurement was performed using a digital caliper in the same way as above and the average value of ten measurements was employed. The experimental results are shown in Table 2.

TABLE 2

| pump voltage E (V) | 13.5 | 13 | 12.5 | 12 |
|---|---|---|---|---|
| transit time $t_p$ (s) | 0.32 | 0.4 | 0.48 | 0.6 |
| moving speed v (mm/s) | 125 | 100 | 83 | 67 |
| distance $X_1$ (mm) | 31.8 | 31.2 | 31.4 | 31 |

As shown in Table 2, the distance $X_1$ corresponding to the actual stop position was different by about 1 mm from the distance $X_0=30$ mm corresponding to the target stop position. However, a difference of this degree is considered to be allowable in a reciprocating channel type PCR device. For example, even if the stop position of the sample 20 to be subjected to PCR is shifted by about 1 mm in the channel, in terms of the adjustment of the design of the processor and the like and the input amount of the sample, it is easy to reduce the length of the sample subjected to PCR such that the length becomes smaller than the length of the channel corresponding to each temperature region by about 1 mm (or several millimeters in view of margin). Further, the reason for why the above shifting of the stop position occurs can be speculated as follows. Since the moving speed v of the sample 20 is calculated based on the transit time for passing through the fluorescence detection region 65, a difference from the moving speed of the sample until the stopping in any temperature region after passing through the fluorescence detection region 65 arises or variation, although in an extremely small range, in the delay time $t_{d3}$ relating to the stopping of the sample 20 occurs. As an example of a measure for compensating for the shifting of the stop position, the waiting time $t_{d2}$ may be determined based on the right side of the equation (6), that is, $X_0/v-t_c$. More specifically, the waiting time $t_{d2}$ may be calculated based on the right side of equation (6): $X_0/v-t_c$ to be basic waiting time, and the temporal correction term $t_k$ may be added so as to determine the waiting time $t_{d2}$ based on the following equation (7)

$$t_{d2}=X_0/v-t_c+t_k \quad (7)$$

In the above, reference was made to the difference in the peak intensity of the fluorescence signal at the beginning of the reaction and when the reaction proceeded to a certain extent (see FIGS. 5 and 6). When a predetermined percentage (for example, 50%) of the difference between the peak intensity of the fluorescence signal and the baseline is set as a threshold value and the transit time $t$, of the fluorescence detection region 65 of the sample 20 is determined based on the threshold value, if a threshold value for the beginning of the reaction is continuously used, there is a possibility that the transit time t, obtained based on the fluorescence signal graph becomes longer than the actual transit time when the reaction proceeds to a certain extent.

Therefore, in a reaction processor according to another embodiment of the present invention, the threshold value for obtaining the transit time $t_p$ may be set as follows. The sample 20 is subjected to a thermal cycle by continuously reciprocating between temperature regions of different set temperatures. Therefore, the CPU 36 may obtain a time-series change of the fluorescence signal for each cycle and obtain the threshold value of the cycle based on the change. Thereby, an appropriate threshold value can be obtained according to the progress of the reaction.

Further, the threshold value of a certain cycle may be obtained based on the time-series change of the fluorescence signal in the previous cycle. The method of obtaining the threshold value of a certain cycle based on the fluorescence signal graph of the cycle as described above requires more rapidity in calculation. Thus, the load on the CPU 36 inevitably becomes large, and in order to reduce the load, the moving speed v of the sample 20 may need to be adjusted to become smaller. Therefore, in order to reduce the load on the control system including the CPU 36, it is effective to obtain the threshold value based on the fluorescence signal graph in the previous cycle. The difference from the fluorescence signal in merely the immediately previous cycle is very small. Thus, the probability that the calculation of the transit time $t_p$ of the sample 20 is affected and, further, the stop position of the sample 20 is greatly shifted is extremely small.

When the threshold value for determining the transit time $t_p$ is fixed to the threshold value for the beginning of the reaction, the following adverse effects may occur. Although the sample 20 moves continuously and reciprocally in the channel, there may be a residue of the sample, which is not subjected to be moved, on the inner wall of the channel 12 in the fluorescence detection region 65. Since there is a possibility that fluorescence is produced also from such a residue of the sample, if the fluorescence is larger than the threshold value for the beginning of the reaction, the baseline may exceed the threshold value for the beginning of the reaction and the passage of the sample 20 may not be detected.

The inventors of the present invention conducted an experiment to obtain knowledge about the difference in stop position of the sample 20 when the way of determining the threshold value was changed. The experimental results are shown in Table 3. In this experiment, in the case where a thermal cycle was applied to a sample 20 containing DNA, a fluorescent probe, and the like so as to attempt the amplification of the actual predetermined DNA, $X_1$, which corresponds to the position where the sample 20 actually stopped when the moving speed v of the sample 20 at the beginning of the reaction and the moving speed v when the reaction proceeded to a certain extent (the latter stage of reaction) were changed, was measured. Distances $X_{01}$ and $X_{02}$, which respectively correspond to target stop positions on the high temperature region side and the low temperature region side, were both set to 30 mm. For the distance $X_1$ corresponding to the actual stop position of the sample, $X_1$ on the high temperature region side was measured so as not to be influenced by the difference in the temperature range. In Table 3, a threshold value being fixed means a case where the threshold for each cycle was fixed to a threshold value for the beginning of the reaction, and a threshold value being variable means a case where the threshold value for each cycle was set to the threshold value for the previous cycle. As can be seen from Table 3, when the threshold value is fixed, there was a difference in $X_1$ between the beginning of the reaction and the latter stage of the reaction. On the other hand, when the threshold value is variable, $X_1$ at the beginning of the reaction is almost the same as that at the latter stage of the reaction. As can be seen from the verification experiment shown in Table 3, setting the threshold value to be variable is very effective in reducing variation in the stop position of the sample 20.

TABLE 3

| | | | pump voltage E(V) | | | |
|---|---|---|---|---|---|---|
| | | | 13.5 | 13 | 12.5 | 12 |
| distance $X_1$ (mm) | threshold value: fixed | moving speed v (mm/s) | 125 | 91 | 80 | 65 |
| | | at the beginning of reaction | 31 | 31 | 31 | 32 |
| | | at the latter stage of reaction | 42 | 37 | 37 | 35 |
| | threshold value: variable | moving speed v (mm/s) | 125 | 95.2 | 83.3 | 66.7 |
| | | at the beginning of reaction | 32 | 31 | 31 | 31 |
| | | at the latter stage of reaction | 31 | 32 | 32 | 31 |

In PCR where predetermined DNA or the like is amplified, there is a case in general where a thermal cycle of about 40 to 50 cycles is applied to a sample containing the predetermined DNA or the like. The time required for reciprocation between a denaturation region (high temperature region) and an annealing and elongation region (low temperature region) of a reaction region is now studied. If it is assumed that the time required for going forward and the time required for coming back are each five seconds, when 50 cycles of the thermal cycle required for PCR are necessary, the time required for moving between the high temperature and low temperature regions can be estimated as 500 seconds. Further, if the time for going forward and the time for coming back can be shortened to about 1 second, the time required for moving between the high temperature and low temperature regions can be estimated to be 100 seconds, and a considerable reduction in time can thus be expected.

Therefore, under the constraints of the control system and each driver, the moving speed v of the sample 20 is required to be increased, and a stable moving speed v is also required to be exhibited as a matter of course. Since the transit time $t_p$ is inversely proportional to the moving speed v of the sample 20, the transit time $t_p$ is desirably small and constant. The transit time t, can be calculated sequentially from the fluorescence signal graph at the time of the movement of the sample 20, and the transit time $t_p$ depends on the increase or decrease of the pump applied voltage E. Therefore, by determining the target value (target transit time) for the transit time $t_p$ and changing the pump voltage E in accordance with a known control method such as P control, PI control, or PID control, the transit time $t_p$ of the sample 20 can be brought close to the target transit time and maintained.

In a reaction processor according to still another embodiment of the present invention, a CPU 36 may be provided in advance with a table that determines the increase or decrease of the pump voltage E according to the difference between the transit time $t_p$ and the target transit time of a sample 20 for passing through a fluorescence detection region 65 of the sample 20 in addition to the PID control or the like. An example of the table is shown in Table 4.

TABLE 4

| transit time $t_p$ (s) | adjustment voltage $\Delta E$ (v) |
|---|---|
| 3-999 | 1.5 |
| 2-3 | 1 |
| 1-2 | 0.5 |
| 0.7-1 | 0.2 |
| 0.6-0.7 | 0.1 |
| 0.5-0.6 | 0 |
| 0.4-0.5 | −0.1 |
| 0.3-0.4 | −0.5 |
| −1-0.3 | −1.5 |

In the table shown in Table 4, as an example, in the case where the standard pump voltage E is set to 12.5 V, when the transit time $t_p$ of the sample 20 falls within a range shown in the left column of Table 4, the corresponding adjustment voltage $\Delta E$ is to be added to the pump voltage E in the next cycle. The target transit time is set to 0.5 seconds to 0.6 seconds in this case. As the performance necessarily required for the reaction processor, the transit time $t_p$ is preferably small (the moving speed v is large). However, there is a case where the transit time $t_p$ that is too small is inappropriate due to restrictions such as the time constant of each driver. In the present embodiment, as an example, since the transmission of a fluorescence signal from the fluorescence detector driver is performed every 0.01 second (100 Hz) and there is also a time constant based on the evaluation and the like of the data of the fluorescence signal by the CPU 36, it is meaningless to set the target transit time to be too small, and the target transit time was set to be about 2 to 10 times larger than to.

Further, since the sample 20 is an aqueous solution, the viscosity of the sample 20 changes depending on the temperature. For example, at high temperature, the viscosity becomes small and easily flows in the channel. Therefore, the condition for the movement of the sample 20 is different between a case where the sample 20 moves from a low temperature region to a high temperature region and a case where the sample 20 moves from the high temperature region to the low temperature region. Therefore, in order to make the transit time $t_p$ of the sample 20 as constant as possible, it is desirable to have separate control according to the moving direction of the sample 20.

In a reaction processor according to still another embodiment of the present invention, when a sample 20 moves from a low temperature region to a high temperature region, based on a first transit time $t_{p1}$ from the low temperature region to the high temperature region in the previous cycle, the pump voltage E of a pump 40 (a pump for moving the sample 20 from the low temperature region to the high temperature region by pressurization or air blowing) in FIG. 2 is changed such that the first transit time $t_{p1}$ thereby converges to the target transit time. On the other hand, when the sample 20 moves from the high temperature region to the low temperature region, based on a second transit time $t_{p2}$ from the high temperature region to the low temperature region, the pump voltage E of a pump 39 (in the same figure, a pump that moves the sample 20 from the high temperature region to the low temperature region) is changed such that the second transit time $t_{p2}$ thereby converges to the target transit time. Further, by performing such control, it is possible to allow each of the transit times to reach the target transit time faster.

Figure 8:
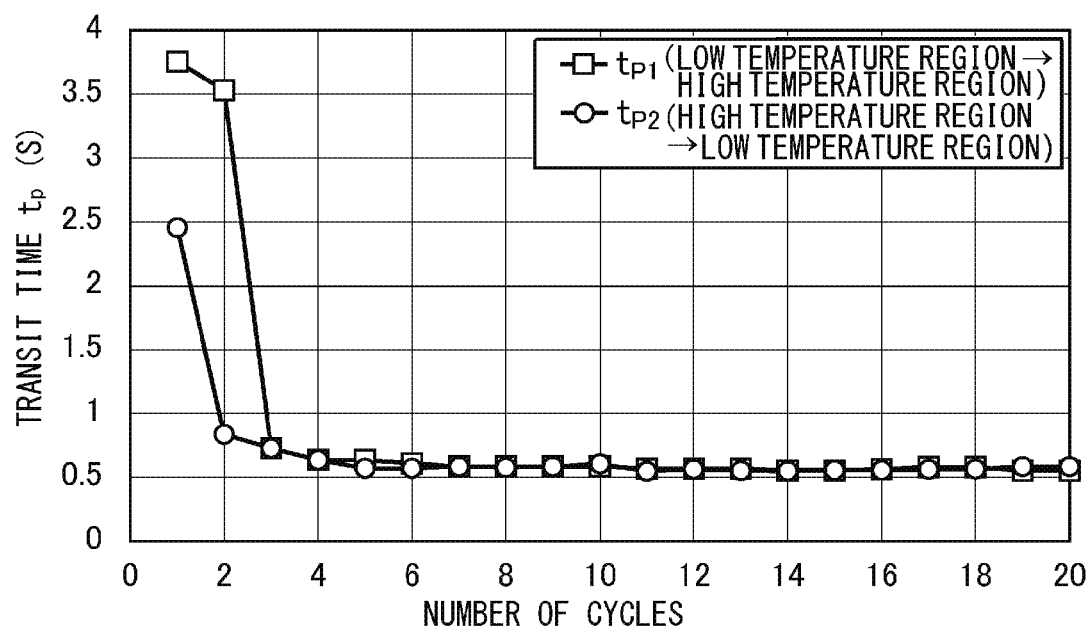
FIG. 8 is a diagram showing the result of an experiment where the transit time of a sample is controlled according to the table of Table 4.

FIG. 8 shows the experimental result of controlling the first transit time $t_{p1}$ and the second transit time $t_{p2}$ of the sample 20 according to the table of Table 4. Regarding the target stop positions, for distances corresponding to the respective target stop positions, the distance corresponding to the target stop position on the high temperature region side and the distance corresponding to the target stop position on the low temperature region side are denoted as $X_{01}$ and $X_{02}$, respectively, and $X_{01}=X_{02}=30$ mm is established. In FIG. 8, the horizontal axis represents the number of cycles of thermal cycles, and the vertical axis represents the transit time. The transit time $t_p$ is inversely proportional to the moving speed v of the sample 20. It can be understood from FIG. 8 that the first transit time $t_{p1}$ and the second transit time $t_{p2}$ are able to be controlled so as to converge to the target transit time (0.5 seconds to 0.6 seconds).

In the above embodiment, the target value of the first transit time $t_{p1}$ and the target value of the second transit time $t_{p2}$ were controlled to be in the same range, and it was confirmed that the sample 20 moved in a reciprocating manner in almost the same transit time as a result. However, the target transit time of the first transit time $t_{p1}$ and the target transit time of the second transit time $t_{p2}$ may be controlled to be different from each other such that the sample 20 is moved in a reciprocating manner while having the first transit time $t_{p1}$ and the second transit time $t_{p2}$ that are different from each other as a result. For example, when there is a tendency that a residue is produced on the inner wall or the like of the channel 12 after passing through the inner wall or the like when the movement from the low temperature region, where the viscosity of the sample 20 is higher, to the high temperature region, an effect can be possible where such a problem is overcome by setting the first transit time $t_{p1}$ relating to the movement from the low temperature region to the high temperature region to be longer than the second transit time $t_{p2}$ such that the sample 20 is moved relatively slowly. Further, given that the moving speed of the sample 20 from the low temperature region to the high temperature region and the moving speed of the sample 20 from the high temperature region to the low temperature region are denoted as $v_1$ and $v_2$, respectively, and that the length of the sample 20 in the channel is denoted as L, calculations of $v_1=L/t_{p1}$ and $v_2=L/t_{p2}$ can be possible using the first transit time $t_{p1}$ and the second transit time $t_{p2}$. From this, independent moving speeds can be used for controlling the moving speed of the sample 20 for the movement from the low temperature region to the high temperature region and from the high temperature region to the low temperature region, respectively. More specifically, in the reaction processor according to another embodiment of the present invention, given that the waiting time when the sample 20 moves from the low temperature region to the high temperature region is set to a first waiting time $t_{d2/1}$ and that the waiting time when the sample 20 moves from the high temperature region to the low temperature region is set to a second waiting time $t_{d2/2}$, the second waiting time $t_{d2/2}$ is set independently of the first waiting time $t_{d2/1}$. Although the method of calculating the first waiting time $t_{d2/1}$ and the second waiting time $t_{d2/2}$ is not limited to this, the first waiting time $t_{d2/1}$ and the second waiting time $t_{d2/2}$ may be calculated separately based on the equation (6), and the first waiting time $t_{d2/1}$ and the second waiting time $t_{d2/2}$ are calculated as shown in the following equations (8) and (9) so as to control the reaction processor based on these waiting times.

$$t_{d2/1}=X_{01}/v_1-t_c \quad (8)$$

$$t_{d2/2}=X_{02}/v_2-t_c \quad (9)$$

According to the reaction processor according to the embodiment as described above, in response to the difference in the moving speed due to the temperature difference of the sample 20 repeatedly reciprocating between the high temperature region and the low temperature region, the sample 20 can be stopped at an appropriate position.

On the other hand, since the fluorescence detection region is provided in a connection channel connecting the high temperature region and the low temperature region, when the sample 20 moves from the low temperature to the high temperature region, the temperature of the sample 20 entering the high temperature region and moving is higher than the temperature of the sample 20 moving near the fluorescence detection region. Thus, the viscosity of the sample 20 moving in the high temperature region becomes low. In that case, the moving speed of the sample 20 moving in the high temperature region is higher than the moving speed of the sample 20 moving near the fluorescence detection region 65 inside the connection region. Since the moving speed of the sample 20, which is one of the consideration factors of the waiting time set for stopping the sample 20 at the target stop position, is determined based on the passage time of the sample 20 passing through the fluorescence detection region, there is a case where the sample 20 stops at a position way past a preset target stop position in the high temperature region. Conversely, when the sample 20 moves from the high temperature region to the low temperature region, there is a case where the sample 20 stops at a position that does not reach the preset target stop position in the low temperature region. Therefore, there is a difference between the stop position when the sample 20 moves from the low temperature region to the high temperature region and the stop position when the sample 20 moves from the high temperature region to the low temperature region.

In the reaction processor according to still another embodiment of the present invention, since the moving speed of the sample 20 is also different in a single process related to the movement from the low temperature region to the high temperature region and from the high temperature region to the low temperature region as described above, a correction coefficient for the moving speed is introduced so as to calculate the first waiting time $t_{d2/1}$ and the second waiting time $t_{d2/2}$. More specifically, the product of the moving speeds $v_1$ and $v_2$ of the sample 20 and their correction coefficients f and g is applied to the equations (8) and (9), and the first waiting time $t_{d2/1}$ and the second waiting time $t_{d2/2}$ are calculated based on the following equations (10) and (11) so as to control the reaction processor based on these waiting times. Further, since the speed of the sample 20 moving in the high temperature region is larger than the speed of the sample 20 moving near the fluorescence detection region 65 in the connection region when the sample 20 moves from the low temperature region to the high temperature region and the speed of the sample 20 moving in the low temperature region becomes smaller than the speed of the sample 20 moving near the fluorescence detection region 65 in the connection region when the sample 20 moves from the high temperature region to the low temperature region, the first waiting time $t_{d2/1}$ and the second waiting time $t_{d2/2}$ are calculated using 1<f and/or g<1 so as to control the reaction processor based on these waiting times.

$$t_{d2/1}=X_{01}/(f^*v_1)-t_c \quad (10)$$

$$t_{d2/2}=X_{02}/(g^*v_2)-t_c \quad (11)$$

Further, in the reaction processor according to still another embodiment of the present invention, instead of introducing the correction coefficient for the moving speed, correction coefficients for the distances $X_{01}$ and $X_{02}$ respectively corresponding to the target stop positions on the high temperature region side and the low temperature region side are introduced so as to calculate the first waiting time $t_{d2/1}$ and the second waiting time $t_{d2/2}$. Since the moving speed is calculated every time the sample 20 passes through the fluorescence detection region 65, it is burdensome to calculate the first waiting time $t_{d2/1}$ and the second waiting time $t_{d2/2}$ in consideration of the correction coefficient each time as described above in some cases. Since the target stop position is represented by a distance specific to the processor or the like, such a burden can be removed if the correction coefficient is taken into consideration before the reaction processing in some cases. However, in any case, a person skilled in the art can appropriately select. More specifically, the product of the distances $X_{01}$ and $X_{02}$ respectively corresponding to the target stop position on the high temperature region side and the target position on the low temperature region side and their correction coefficients k and h are applied to the equations (8) and (9), and the first waiting time $t_{d2/1}$ and the second waiting time $t_{d2/2}$ are calculated based on the following equations (12) and (13) so as to control the reaction processor based on these waiting times. Further, since the speed of the sample 20 moving in the high temperature region becomes larger than the speed of the sample 20 moving near the fluorescence detection region 65 in the connection region when the sample 20 moves from the low temperature to the high temperature region, the sample 20 tends to stop beyond $X_{01}$ corresponding to the target stop position. Also, since the speed of the sample 20 moving in the low temperature region is lower than the speed of the sample 20 moving near the fluorescence detection region 65 in the connection region when the sample 20 moves from the high temperature region to the low temperature region, the sample 20 tends to stop before $X_{02}$ corresponding to the target stop position. Based on these, the first waiting time $t_{d2/1}$ and the second waiting time $t_{d2/2}$ are calculated using k<1 and/or 1<h so as to control the reaction processor based on these waiting times.

$$t_{d2/1}=(k^*X_{01})/v_1-t_c \quad (12)$$

$$t_{d2/2}=(h^*X_{02})/v_2-t_c \quad (13)$$

According to the reaction processor according to the embodiment as described above, even when the moving speed of the sample 20 in the fluorescence detection region 65 is different from that inside the channel 12 in the high temperature region or when the moving speed of the sample 20 in the fluorescence detection region 65 is different from that inside the channel 12 in the low temperature region, the stop position of the sample 20 can be corrected, and, further, the sample 20 can be accurately stopped at an appropriate position in each temperature region.

On the other hand, since the channel 12 is not wet with the sample solution and is dry when the sample 20 moves for the first time, the environment of the channel 12 is different, for example, in the case where the sample 20 moves from the low temperature region to the high temperature region for the first time and in the case where the sample 20 moves from the low temperature region to the high temperature region for the second time or thereafter. Therefore, at the time of the second movement from the low temperature region to the high temperature region, the pump voltage E does not need to be adjusted based on the transit time $t_p$ required for the previous (first) movement (operated with a standard pump voltage E (e.g., E=12.5 V)).

More specifically, given that a state in which the sample 20 is in the low temperature region or the high temperature region is expressed as "low temperature (n)" or "high temperature (n)", where n is the number of cycles (n is an integer), when a cycle "low temperature (0)→high temperature (0)→low temperature (1)→high temperature (1)→low temperature (2)→high temperature (2)→low temperature (3)→high temperature (3)→ . . . low temperature (n) high temperature (n)→ . . . " is assumed, the pump may be operated at the standard pump voltage E=12.5 V for the three movements: low temperature (0)→high temperature (0)→low temperature (1)→high temperature (1), the adjustment voltage ΔE corresponding to the transit time $t_{p2}$ required for the movement of high temperature (0)→low temperature (1) may be added for the movement of high temperature (1)→low temperature (2), and the adjustment voltage ΔE corresponding to the transit time $t_{p1}$ required for the movement of low temperature (1)→high temperature (1) may be added for the movement of low temperature (2)→high temperature (2). In general, while having n being an integer of 1 or more, the adjustment voltage ΔE corresponding to the transit time $t_{p2}$ required for the movement of high temperature (n−1)→low temperature (n) may be added for the movement of high temperature (n)→low temperature (n+1), and the adjustment voltage ΔE corresponding to the transit time $t_{p1}$ required for the movement of low temperature (n)→high temperature (n) may be added for the movement of low temperature (n+1)→high temperature (n+1). In contrast, when a cycle "high temperature (0)→low temperature (0)→high temperature (1)→low temperature (1)→high temperature (2)→low temperature (2)→high temperature (3)→low temperature (3)→ . . . high temperature (n)→low temperature (n)→ . . . " is assumed, the pump may be operated at the standard pump voltage E=12.5 V for the three movements: high temperature (0)→low temperature (0)→high temperature (1)→low temperature (1), the adjustment voltage ΔE corresponding to the transit time $t_{p1}$ required for the movement of low temperature (0)→high temperature (1) may be added for the movement of low temperature (1)→high temperature (2), and the adjustment voltage ΔE corresponding to the transit time $t_{p2}$ required for the movement of high temperature (1)→low temperature (1) may be added for the movement of high temperature (2)→low temperature (2). In general, while having n being an integer of 1 or more, the adjustment voltage ΔE corresponding to the transit time $t_{p1}$ required for the movement of low temperature (n−1)→high temperature (n) may be added for the movement of low temperature (n)→high temperature (n+1), and the adjustment voltage ΔE corresponding to the transit time $t_{p2}$ required for the movement of high temperature (n)→low temperature (n) may be added for the movement of high temperature (n+1)→low temperature (n+1).

According to a reaction processor according to such an embodiment, by controlling the pump 40 based on a first transit time $t_{p1}$, which is required when moving from a low temperature region to a high temperature region, when moving from the low temperature region to the high temperature region, and controlling the pump 39 based on a second transit time $t_{p2}$, which is required when moving from the high temperature region to the low temperature region, when moving from the high temperature region to the low temperature region, control that is suitable for the temperature and viscosity of a sample 20 used for each movement can be performed, and, without requiring a quick and complicated mechanism, it is possible to reach an appropriate target transit time and consequently a target moving speed and to set a first transit time $t_{p1}$ and a second transit time $t_{p2}$ that are different depending on the situation as well. Further, by not controlling the movement for 1.5 reciprocations from the start of the thermal cycle, a transit time under an environment where conditions are significantly different due to influence such as the wettability and dryness of the channel 12 in the initial state can be excluded from the parameters for the control, and the target transit time can be reached more accurately and promptly.

As explained above, according to the reaction processor 30 according to the above-described series of embodiments, by instructing the first pump driver 41 and the second pump driver 42 of the liquid feeding system 37 to stop the sample 20 when the waiting time $t_{d2}$ (or the first waiting time $t_{d2/1}$ and the second waiting time $t_{d2/2}$) defined in the above equations (6) to (13) has passed from the time when the passage of the sample 20 through the fluorescence detection region 65 is detected, the sample 20 can be accurately stopped at a predetermined position in a temperature range. Further, according to the reaction processor 30 according to these embodiments, even when the moving speed v of the sample 20 varies due to variation in various physical property values, the sample can always be stopped at a predetermined position, and stable PCR can thus be performed.

In the reaction processor 30 according to these embodiments, by using the fluorescence detector 50, which is responsible for progress management of real time PCR, as a means for positioning the sample 20, it is not necessary to add any other optical measurement system, contributing to the downsizing of the processor, and it is also possible to reduce the manufacturing cost of the processor.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

What is claimed is:
1. A reaction processor comprising:
a reaction processing vessel in which a channel where a sample moves is formed;
a liquid feeding system that moves and stops the sample in the channel;
a temperature control system that provides a first temperature region maintained at a first temperature and a second temperature region maintained at a second temperature lower than the first temperature in the channel;
a detection system that detects the sample passing through a detection region that is set between the first temperature region and the second temperature region of the channel; and
a control unit that controls the liquid feeding system based on a signal detected by the detection system,
wherein when the sample moves from the second temperature region to the first temperature region, the control unit instructs the liquid feeding system to stop the sample when a first waiting time $t_{d2/1}$ has passed from the time when the passage of a rear end portion of the sample through the detection region is detected by the detection system,
wherein when the sample moves from the first temperature region to the second temperature region, the control unit instructs the liquid feeding system to stop the sample when a second waiting time $t_{d2/2}$ has passed from the time when the passage of the rear end portion of the sample through the detection region is detected by the detection system, wherein given that when the sample moves from the second temperature region to the first temperature region, the moving speed of the sample in the detection region is denoted as a first moving speed $v_1$, the distance between an end portion of the sample stopping at a predetermined position in the channel that is closest to the detection region and the center of the detection region is denoted as $X_{01}$, and $\alpha$ is defined as a correction coefficient that satisfies $\alpha<1$, the first waiting time $t_{d2/1}$ is defined by the following equation:

$$t_{d2/1}=\alpha*(X_{01}/v_1)-t_c,$$

wherein given that when the sample moves from the first temperature region to the second temperature region, the moving speed of the sample in the detection region is denoted as a second moving speed $v_2$, the distance between an end portion of the sample stopping at a predetermined position in the channel that is closest to the detection region and the center of the detection region is denoted as $X_{02}$, and $\beta$ is defined as a correction coefficient that satisfies $\beta<1$, the second waiting time $t_{d2/2}$ is defined by the following equation:

$$t_{d2/2}=\beta*(X_{02}/v_2)-t_c, \text{ and}$$

wherein $t_c$ is time corresponding to the difference between the time when the rear end portion of the sample has actually passed through the detection region and the time when the detection unit has detected the passage of the rear end portion of the sample through the detection region.

2. The reaction processor according to claim 1, wherein the sample includes DNA, a PCR reagent, and a reagent that emits fluorescence, wherein the detection system includes a fluorescence detector for detecting fluorescence emitted from the sample, and wherein given that:

the time the sample takes to pass through the detection region when the sample moves from the second temperature region to the first temperature region is denoted as a first transit time $t_{p1}$; and the time the sample takes to pass through the detection region when the sample moves from the first temperature region to the second temperature region is denoted as a second transit time $t_{p2}$, the first transit time $t_{p1}$ and the second transit time $t_{p2}$ are defined by the difference between the time when a leading end part of the sample enters the detection region and the time when the rear end part of the sample exists the detection region, the control unit obtains the first transit time $t_{p1}$ and the second transit time $t_{p2}$ based on the signal from the fluorescence detector or a value obtained by performing predetermined arithmetic processing on the signal and on a predetermined threshold value, and the control unit calculates the first moving speed $v_1=L/t_{p1}$ based on the first transit time $t_{p1}$ and the length L of the sample and the second moving speed $v_2=L/t_{p2}$ based on the second transit time $t_{p2}$ and the length L of the sample.

3. The reaction processor according to claim 2, wherein the control unit changes the threshold value according to the progress of the reaction of the sample.

4. The reaction processor according to claim 2, wherein the control unit controls the liquid feeding system such that the first transit time $t_{p1}$ and the second transit time $t_{p2}$ become predetermined target transit times.

5. The reaction processor according to claim 1, wherein the detection system is a fluorescence detector provided such that the fluorescence detector can detect fluorescence emitted from the sample passing through the detection region.

6. The reaction processor according to claim 2, wherein the first transit time $t_{p1}$ is 0.30 to 0.97 seconds.

7. The reaction processor according to claim 1, wherein $t_c$ is 0.19 to 0.21 seconds.

8. The reaction processor according to claim 1, wherein the liquid feeding system includes a micro blower pump.

9. The reaction processor according to claim 8, wherein voltage applied to the micro blower pump is adjusted between −1.5 V to +1.5 V with respect to reference voltage E.

* * * * *